United States Patent [19]
Zimmerman

[11] Patent Number: 5,941,820
[45] Date of Patent: Aug. 24, 1999

[54] MEDICAL DATA DISPLAY METHOD

[76] Inventor: Steven Zimmerman, 4151 Bay Front Rd., Mobile, Ala. 36605

[21] Appl. No.: 08/888,008

[22] Filed: Jul. 3, 1997

Related U.S. Application Data

[63] Continuation-in-part of application No. 08/519,508, Aug. 25, 1995, abandoned, which is a continuation-in-part of application No. 08/176,475, Jan. 3, 1994, abandoned.

[51] Int. Cl.$^6$ ........................................................ A61B 5/04
[52] U.S. Cl. ............................................................. 600/300
[58] Field of Search ........................... 128/898, 920–925; 600/300, 481, 515, 544–547

[56] References Cited

U.S. PATENT DOCUMENTS

| | | |
|---|---|---|
| 3,322,954 | 5/1967 | Bell et al. . |
| 3,980,075 | 9/1976 | Heule . |
| 4,463,762 | 8/1984 | Rubens . |
| 4,519,395 | 5/1985 | Hrushesky . |
| 4,545,388 | 10/1985 | John . |
| 4,583,524 | 4/1986 | Hutchins . |
| 4,844,086 | 7/1989 | Duffy . |
| 5,199,439 | 4/1993 | Zimmermann et al. . |
| 5,215,098 | 6/1993 | Steinhaus et al. . |
| 5,564,433 | 10/1996 | Thornton . |
| 5,713,350 | 2/1998 | Yokota et al. ......................... 600/300 |

OTHER PUBLICATIONS

Brown, Lonnie D., Steven M. Zimmermann Ph.D., S. S. Brown, "Abstract–Medical Instrumentation + Quality Control=Earling Warning of Patient Instability", Association for the Advancement of Medical Instrumentation 25th Annual Meeting and Exposition 1990, p. 17.

Laffel, Glen, Robert Luttman, and Steven M. Zimmerman (1993), "Using Control Charts to Analyze Serial Patent–Related Data", Submitted Sep. 26, 1993.

Al Pfadt and Donald J. Wheeler (1993), "Control Charts–Powerful Tools in a Clinical Setting," SPC Ink, 1–.

Zimmerman, Steven M., Robert N. Zimmerman, Lonnie D. Brown, and Shannon S. Brown, 91992) "Using Moving Average Process Control Charts in Biomedical Applications," Proceedings—Ninth International Conference on Israel Society of Quality Assurance, 1992, Nov. 1992, 761–764.

(List continued on next page.)

*Primary Examiner*—John P. Lacyk
*Assistant Examiner*—Samuel Gilbert

[57] ABSTRACT

The invention is a method of measuring patient data, determining statistics from the data; determining measures of variation within the data, determining from the measures of variation a measure of homeostasis, modifying control chart limits based on the determined measure of homeostasis and displaying the statistic on the modified control chart. In addition, the control charts are modified as data varies over time in statistically significant groups as determined by the user and the modification of the limits is repeated so that the patient's real time change in condition is constantly reflected in modified control charts. Records of the changes in the chart limits and data are maintained for consistency. Patient specific data received from a monitor are thereby modified to reflect the level of consistency in data received. The date include specific biological rhythms such as: pulse, oxygen content in the blood, blood pressure, and other bodily functions capable of being monitored. By determining the amount of consistency (or similarity) within consecutive subgroups of data (auto correlation or serial correlation) significant changes in the body may be identified relative to the time when consistency changes. The data are coordinated by time and subgroup number. The results are applied to control chart data (1) to obtain statistical results comparable to statistically independent control chart data, (2) to correct limits for control chart data, (3) to correct the plotting of data for control charts and (4) to determine when the prior three actions should be taken and for treating and diagnosing patients.

26 Claims, 23 Drawing Sheets

OTHER PUBLICATIONS

Zimmerman, Steven M., Lonnie D. Brown, Shannon S. Brown, and Richard L. Goldhammer, M.D. (1990), "Quality Control Charts for Patient Data." The 18th International Conference on Israel Society for Quality Assurance Transactions Nov. 26–29, 1990 Jerusalem.

Zimmerman, Steven M., Lonnie Brown, Shannon Brown, and Robert N. Zimmerman (1992) "Using the Theory of Runs in a Biomedical Application," 46th Annual Quality Control Congress Transactions May 18–20, p903–908.

Zimmerman, Steven M., Lonnie Brown, ,Shannon Brown, and Leroy Alexander (1990), "Human Body Function Control Charts for the Physician," 44th Annual Quality Congress Transactions May 14–16, pp. 408–412.

| 14 | 15 | 16 | 17 | 18 | 19 |
|---|---|---|---|---|---|
| Heart Rate | 120.000 | 150.000 | 5.000 | 1.000 | | |
| 14:45: 8 | 143.000 | 141.000 | 141.000 | 140.000 | 140.000 | F9 |
| 14:45:50 | 140.000 | 141.000 | 141.000 | 140.000 | 142.000 |
| 14:45-55 | 143.000 | 143.000 | 144.000 | 144.000 | 144.000 |
| 14:46- 0 | 143.000 | 146.000 | 144.000 | 145.000 | 149.000 |
| 14:46: 5 | 148.000 | 145.000 | 145.000 | 144.000 | 144.000 |
| 14:46:10 | 143.000 | 143.000 | 144.000 | 144.000 | 143.000 |
| 14:46:15 | 141.000 | 141.000 | 141.000 | 141.000 | 140.000 |
| 14:46-20 | 139.000 | 140.000 | 139.000 | 140.000 | 142.000 |
| 14.-46:25 | 142.000 | 142.000 | 142.000 | 141.000 | 140.000 |
| 14:46:30 | 138.000 | 138.000 | 138.000 | 138.000 | 140.000 |
| 14:46:35 | 138.000 | 142.000 | 142.000 | 141.000 | 139.000 |
| 14:46:41 | 137.000 | 137.000 | 136.000 | 135.000 | 134.000 |
| 14:46:45 | 133.000 | 134.000 | 133.000 | 133.000 | 132.000 |
| 14:46:50 | 133.000 | 133.000 | 133.000 | 132.000 | 132.000 |
| 14:46:56 | 132.000 | 133.000 | 134.000 | 135.000 | 135.000 |
| 14:47:1 | 136.000 | 136.000 | 136.000 | 136.000 | 136.000 |
| 14:47:5 | 136.000 | 136.000 | 136.000 | 136.000 | 135.000 |
| 14:47: 9 | 135.000 | 134.000 | 134.000 | 134.000 | 133.000 |
| 14:47:14 | 137.000 | 137.000 | 137.000 | 137.000 | 138.000 |
| 14:47:19 | 138.000 | 137.000 | 137.000 | 136.000 | 137.000 |
| 14:47:23 | 135.00'0 | 135.000 | 134.000 | 134.000 | 136.000 |
| 14:47:28 | 136.000 | 137.000 | 136.000 | 136.000 | 136.000 | F9 |
| 14:47:34 | 136.000 | 136.000 | 136.000 | 136.000 | 137.000 |
| 14:47:40 | 138.000 | 139.000 | 138.000 | 138.000 | 138.000 |
| 14:47:45 | 137.000 | 136.000 | 136.000 | 135.000 | 135.000 |
| 14:47:49 | 134.000 | 134.000 | 134.000 | 134.000 | 134.000 |
| 14:47:55 | 136.000 | 136.000 | 137.000 | 137.000 | 137.000 |
| 14:47:59 | 136.000 | 134.000 | 132.000 | 130.000 | 130.000 |
| 14:48: 5 | 130.000 | 129.000 | 130.000 | 130.000 | 130.000 |
| 14:48: 9 | 130.000 | 130.000 | 130.000 | 131.000 | 131.000 |
| 14:48:14 | 132.000 | 132.000 | 133.000 | 132.000 | 133.000 |
| 14:48:19 | 133.000 | 132.000 | 133.000 | 132.000 | 132.000 |
| 14:48:24 | 131.000 | 131.000 | 132.000 | 132.000 | 132.000 |
| 14:48:28 | 132.000 | 133.000 | 133.000 | 133.000 | 133.000 |
| 14:48:34 | 131.000 | 131.000 | 131.000 | 131.000 | 132.000 |
| 14:48:39 | 130.000 | 128.000 | 128.000 | 130.000 | 132.000 |
| 14:48:42 | 133.000 | 133.000 | 134.000 | 133.000 | 134.000 |
| 14:48:48 | 134.000 | 134.000 | 133.000 | 134.000 | 134.000 |
| 14:48:53 | 134.000 | 134.000 | 134.000 | 134.000 | 134.000 |
| 14:48:58 | 134.000 | 134.000 | 134.000 | 134.000 | 134.000 |
| 14-49: 2 | 134.000 | 133.000 | 134.000 | 134.000 | 135.000 |
| 14:49: 8 | 136.000 | 136.000 | 137.000 | 136.000 | 136.000 |
| 14:49:13 | 136.000 | 136.000 | 136.000 | 135.000 | 136.000 |
| 14:49:18 | 136.000 | 137.000 | 138.000 | 139.000 | 140.000 |
| 14-49:24 | 142.000 | 143.000 | 143.000 | 143.000 | 144.000 |
| 14:49:28 | 143.000 | 142.000 | 141.000 | 139.000 | 138.000 |
| 14:49:33 | 137.000 | 137.000 | 137.000 | 136.000 | 135.000 |
| 14:49:39 | 134.000 | 134.000 | 133.000 | 132.000 | 132.000 |
| 14-49:44 | 131.000 | 132.000 | 132.000 | 132.000 | 134.000 |
| 14:49:49 | 134.000 | 133.000 | 133.000 | 131.000 | 131.000 |
| 14:49:!->4 | 131.000 | 131.000 | 132.000 | 132.000 | 132.000 |
| 14:49:59 | 131.000 | 131.000 | 130.000 | 130.000 | 130.000 |
| 14:50: 4 | 130.000 | 130.000 | 131.000 | 134.000 | 135.000 |
| 14:50: 9 | 134.000 | 133.000 | 130.000 | 129.000 | 127.000 |
| 14-.50:14 | 125.000 | 125.000 | 125.000 | 124.000 | 124.000 |

*Fig. 2 (a)*

| 14 | 15 | 16 | 17 | 18 | 19 |
|---|---|---|---|---|---|
| 14:50:20 | 125.000 | 128.000 | 131.000 | 129.000 | 128.000 |
| 14:50:25 | 129.000 | 129.000 | 130.000 | 129.000 | 129.000 |
| 14:50:30 | 127.000 | 127.000 | 128.000 | 128.000 | 128.000 |
| 14:50:35 | 129.000 | 128.000 | 128.000 | 128.000 | 128.000 |
| 14:50:41 | 128.000 | 127.000 | 128.000 | 128.000 | 129.000 |
| 14:50:46 | 128.000 | 128.000 | 127.000 | 127.000 | 128.000 |
| 14:50:51 | 129.000 | 129.000 | 130.000 | 129.000 | 131.000 |
| 14:50:56 | 130.000 | 131.000 | 130.000 | 131.000 | 132.000 |
| 14:51: 0 | 133.000 | 132.000 | 133.000 | 132.000 | 132.000 |
| 14:51: 6 | 132.000 | 131.000 | 132.000 | 131.000 | 132.000 |
| 14:51:11 | 131.000 | 131.000 | 131.000 | 130.000 | 130.000 |
| 14:51:15 | 129.000 | 129.000 | 128.000 | 129.000 | 130.000 |
| 14:51:21 | 132.000 | 133.000 | 133.000 | 132.000 | 131.000 |
| 14:51:26 | 130.000 | 129.000 | 130.000 | 130.000 | 130.000 |
| 14:51:31 | 131.000 | 133.000 | 134.000 | 136.000 | 137.000 |
| 14:51:36 | 139.000 | 141.000 | 140.000 | 140.000 | 139.000 |
| 14:51:40 | 139.000 | 139.000 | 138.000 | 138.000 | 136.000 |
| 14:51:46 | 133.000 | 133.000 | 131.000 | 130.000 | 130.000 |
| 14:51:52 | 130.000 | 130.000 | 131.000 | 131.000 | 131.000 |
| 14:51:55 | 132.000 | 131.000 | 131.000 | 131.000 | 130.000 |
| 14:52: 1 | 130.000 | 131.000 | 130.000 | 130.000 | 129.000 |
| 14:52: 6 | 129.000 | 129.000 | 128.000 | 129.000 | 129.000 |
| 14:52:12 | 129.000 | 128.000 | 128.000 | 127.000 | 126.000 |
| 14:52:17 | 125.000 | 126.000 | 125.000 | 126.000 | 126.000 |
| 14:52:22 | 128.000 | 128.000 | 129.000 | 129.000 | 129.000 |
| 14:52:26 | 130.000 | 129.000 | 128.000 | 129.000 | 130.000 |
| 14:52:32 | 131.000 | 131.000 | 131.000 | 131.000 | 131.000 |
| 14:52:38 | 131.000 | 131.000 | 131.000 | 130.000 | 130-000 |
| 14:52:43 | 131.000 | 132.000 | 132.000 | 133.000 | 132.000 |
| 14:52:48 | 132.000 | 131.000 | 131.000 | 132.000 | 132.000 |
| 14:52:53 | 131.000 | 132.000 | 131.000 | 132.000 | 131.000 |
| 14:52:58 | 131.000 | 131.000 | 132.000 | 132.000 | 132.000 |
| 14:53: 4 | 131.000 | 131.000 | 131.000 | 131.000 | 131.000 |
| 14:53: 9 | 132.000 | 132.000 | 133.000 | 133.000 | 133.000 |
| 14:53:14 | 133.000 | 132.000 | 133.000 | 133.000 | 132.000 |
| 14:53:18 | 132.000 | 132.000 | 133.000 | 133.000 | 134.000 |
| 14:53:24 | 134.000 | 134.000 | 133.000 | 133.000 | 133-000 |
| 14:53:29 | 133.000 | 132.000 | 131.000 | 131.000 | 131.000 |
| 14:53:34 | 131.000 | 131.000 | 129.000 | 129.000 | 129-000 |
| 14:53:39 | 129.000 | 129.000 | 129.000 | 129.000 | 130.000 |
| 14:53:44 | 126.000 | 127.000 | 129.000 | 131.000 | 131.000 |
| 14:53:48 | 130.000 | 130.000 | 130.000 | 130.000 | 131.000 |
| 14:53:53 | 130.000 | 130.000 | 130.000 | 129.000 | 130-000 |
| 14:53:58 | 131.000 | 130.000 | 131.000 | 130.000 | 131.000 |
| 14:54: 4 | 132.000 | 133.000 | 133.000 | 133.000 | 132.000 |
| 14:54: 8 | 130.000 | 130.000 | 131.000 | 130.000 | 130-000 |
| 14:54:13 | 130.000 | 130.000 | 130.000 | 130.000 | 130-000 |
| 14:54:18 | 129.000 | 129.000 | 128.000 | 128.000 | 127.000 |
| 14:54:23 | 128.000 | 129.000 | 131.000 | 131.000 | 132.000 |
| 14:54:28 | 131.000 | 131.000 | 130.000 | 130.000 | 129-000 |
| 14:54:34 | 128.000 | 128.000 | 129.000 | 129.000 | 129-000 |
| 14:54:39 | 129.000 | 129.000 | 128.000 | 128.000 | 128.000 |
| 14:54:44 | 129.000 | 130.000 | 131.000 | 133.000 | 134.000 |
| 14:54:49 | 135.000 | 135.000 | 135.000 | 136.000 | 135.000 |
| 14:54:54 | 134.000 | 135.000 | 134.000 | 133.000 | 132.000 |
| 14:55: 0 | 132.000 | 131.000 | 131.000 | 131.000 | 131.000 |

05TRUNC.wk1
```
                     A    B
Average:            97   97
Sigma:               3    3
Autocorrelation:     0    0
Initial observation:
```

| Subgro | Data 1 | 2 | 3 | 4 | 5 | Xj | S | 1 | 2 | 3 | 4 | SUM |
|---|---|---|---|---|---|---|---|---|---|---|---|---|
| 1 | 96 | 99 | 96 | 96 | 103 | 98.0 | 3.1 | 3 | 3 | 0 | 7 | 13 |
| 2 | 102 | 93 | 98 | 98 | 94 | 97.0 | 3.6 | 9 | 5 | 0 | 4 | 18 |
| 3 | 96 | 99 | 100 | 97 | 94 | 97.2 | 2.4 | 3 | 1 | 3 | 3 | 10 |
| 4 | 95 | 97 | 94 | 99 | 101 | 97.2 | 2.9 | 2 | 3 | 5 | 2 | 12 |
| 5 | 97 | 99 | 103 | 92 | 103 | 98.8 | 4.6 | 2 | 4 | 11 | 11 | 28 |
| 6 | 98 | 100 | 100 | 95 | 96 | 97.8 | 2.3 | 2 | 0 | 5 | 1 | 8 |
| 7 | 99 | 91 | 94 | - | 102 | 97.2 | 4.5 | 8 | 3 | 6 | 2 | 19 |
| 8 | 92 | 97 | 96 | 95 | 93 | 94.6 | 2.1 | 5 | 1 | 1 | 2 | 9 |
| 9 | 98 | 98 | 99 | - | 97 | 98.6 | 1.5 | 0 | 1 | 2 | 4 | 7 |
| 10 | 106 | 96 | 101 | - | 100 | 101.0 | 3.6 | 10 | 5 | 1 | 2 | 18 |
| 11 | 93 | 96 | 100 | 99 | 99 | 97.4 | 2.9 | 3 | 4 | 1 | 0 | 8 |
| 12 | 103 | 94 | 91 | 95 | 96 | 95.2 | 4.9 | 12 | 0 | 4 | 1 | 17 |
| 13 | 98 | 100 | 96 | - | 97 | 99.0 | 3.2 | 2 | 4 | 8 | 7 | 21 |
| 14 | 93 | 101 | 95 | 99 | 97 | 97.0 | 3.2 | 8 | 6 | 4 | 2 | 20 |
| 15 | 97 | 94 | 96 | 94 | 95 | 95.2 | 1.3 | 3 | 2 | 2 | 1 | 8 |
| 16 | 98 | 99 | 94 | 95 | 96 | 96.4 | 2.1 | 1 | 5 | 1 | 1 | 8 |
| 17 | 106 | 90 | 100 | 98 | 99 | 98.2 | 5.8 | 16 | 10 | 4 | 3 | 33 |
| 18 | 97 | 93 | 102 | 92 | 90 | 94.8 | 4.8 | 4 | 9 | 10 | 2 | 25 |
| 19 | 98 | 94 | 100 | 92 | 99 | 96.6 | 3.4 | 4 | 6 | 8 | 7 | 25 |
| 20 | 104 | 97 | 103 | - | 95 | 99.8 | 3.8 | 7 | 6 | 3 | 5 | 21 |
| 21 | 101 | 95 | 99 | - | 95 | 98.2 | 3.0 | 6 | 4 | 2 | 6 | 15 |
| 22 | 99 | 98 | 100 | 99 | 95 | 98.2 | 1.9 | 1 | 2 | 1 | 4 | 8 |
| 23 | 98 | 97 | 97 | 99 | 98 | 97.8 | 0.8 | 1 | 0 | 2 | 1 | 4 |
| 24 | 97 | 98 | 100 | 94 | 95 | 96.8 | 2.4 | 1 | 2 | 6 | 1 | 10 |
| 25 | 95 | 98 | 100 | 93 | 95 | 96.2 | 2.8 | 3 | 2 | 7 | 2 | 14 |
| 26 | 94 | 96 | 100 | 99 | 96 | 97.0 | 2.4 | 2 | 4 | 1 | 3 | 10 |
| 27 | 92 | 90 | 93 | - | 104 | 95.8 | 5.9 | 2 | 3 | 7 | 4 | 16 |
| 28 | 98 | 97 | 100 | - | 94 | 97.8 | 2.5 | 1 | 3 | 0 | 6 | 10 |
| 29 | 99 | 87 | 92 | 90 | 103 | 94.2 | 6.6 | 12 | 5 | 2 | 13 | 32 |
| 30 | 96 | 93 | 98 | 97 | 101 | 97.0 | 2.9 | 3 | 5 | 1 | 4 | 13 |
| 31 | 101 | 96 | 92 | 99 | 100 | 97.6 | 3.6 | 5 | 4 | 7 | 1 | 17 |
| 32 | 96 | 102 | 98 | - | 101 | 99.6 | 2.5 | 6 | 4 | 3 | 0 | 13 |
| 33 | 98 | 92 | 99 | 95 | 98 | 96.4 | 2.9 | 6 | 7 | 4 | 3 | 20 |
| 34 | 95 | 94 | 101 | 97 | 98 | 97.0 | 2.7 | 1 | 7 | 4 | 1 | 13 |
| 35 | 90 | 95 | 93 | 93 | 99 | 94.0 | 3.3 | 5 | 2 | 0 | 6 | 13 |
| 36 | 95 | 100 | 98 | 88 | 95 | 95.2 | 4.5 | 5 | 2 | 10 | 7 | 24 |
| 37 | 95 | 101 | 90 | 94 | 103 | 96.6 | 5.3 | 6 | 11 | 4 | 9 | 30 |
| 38 | 96 | 100 | 97 | 99 | 102 | 98.8 | 2.4 | 4 | 3 | 2 | 3 | 12 |
| 39 | 98 | 97 | 101 | 99 | 101 | 99.2 | 1.8 | 1 | 4 | 2 | 2 | 9 |
| 40 | 93 | 94 | 95 | 97 | 97 | 95.2 | 1.8 | 1 | 1 | 2 | 0 | 4 |
| 41 | 101 | 98 | 96 | 96 | 97 | 97.6 | 2.1 | 3 | 2 | 0 | 1 | 6 |
| 42 | 99 | 98 | 94 | - | 94 | 97.0 | 2.8 | 1 | 4 | 6 | 6 | 17 |
| 43 | 97 | 92 | 100 | - | 97 | 97.2 | 3.3 | 5 | 8 | 0 | 3 | 16 |
| 44 | 99 | 98 | 92 | 97 | 98 | 96.8 | 2.8 | 1 | 6 | 5 | 1 | 13 |
| 45 | 102 | 99 | 98 | 94 | 100 | 98.6 | 3.0 | 3 | 1 | 4 | 6 | 14 |
| 46 | 96 | 96 | 97 | -- | 92 | 96.6 | 3.6 | 0 | 1 | 5 | 10 | 16 |

*Fig. 4 (a)*

| | | | | | | | | | | | | |
|---|---|---|---|---|---|---|---|---|---|---|---|---|
| 47 | 91 | 95 | 103 | 93 | 102 | 96.8 | 5.4 | 4 | 8 | 10 | 9 | 31 |
| 48 | 96 | 102 | 98 | 97 | 98 | 98.2 | 2.3 | 6 | 4 | 1 | 1 | 12 |
| 49 | 95 | 99 | 90 | 94 | 103 | 96.2 | 5.0 | 4 | 9 | 4 | 9 | 26 |
| 50 | 96 | 102 | 96 | 98 | 90 | 96.4 | 4.3 | 6 | 6 | 2 | 8 | 22 |
| 51 | 98 | 97 | 97 | 95 | 96 | 96.6 | 1.1 | 1 | 0 | 2 | 1 | 4 |
| 52 | 99 | 97 | 94 | 94 | 100 | 96.8 | 2.8 | 2 | 3 | 0 | 6 | 11 |
| 53 | 101 | 94 | 104 | 95 | 98 | 98.4 | 4.2 | 7 | 10 | 9 | 3 | 29 |
| 54 | 93 | 99 | 94 | 99 | 92 | 95.4 | 3.4 | 6 | 5 | 5 | 7 | 23 |
| 55 | 95 | 99 | 92 | 93 | 97 | 95.2 | 2.9 | 4 | 7 | 1 | 4 | 16 |
| 56 | 93 | 94 | 102 | - | 95 | 97.0 | 4.2 | 1 | 8 | 1 | 6 | 16 |
| 57 | 92 | 92 | 96 | 96 | 100 | 95.2 | 3.3 | 0 | 4 | 0 | 4 | 8 |
| 58 | 99 | 92 | 98 | - | 101 | 98.2 | 3.7 | 7 | 6 | 3 | 0 | 16 |
| 59 | 100 | 99 | 100 | - | 98 | 99.4 | 0.9 | 1 | 1 | 0 | 2 | 4 |
| 60 | 96 | 95 | 100 | 93 | 97 | 96.2 | 2.6 | 1 | 5 | 7 | 4 | 17 |
| 61 | 98 | 98 | 98 | - | 97 | 98.4 | 1.5 | 0 | 0 | 3 | 4 | 7 |
| 62 | 101 | 96 | 96 | 91 | 94 | 95.6 | 3.6 | 5 | 0 | 5 | 3 | 13 |
| 63 | 101 | 97 | 95 | 98 | 93 | 96.8 | 3.0 | 4 | 2 | 3 | 5 | 14 |
| 64 | 97 | 97 | 95 | - | 103 | 98.6 | 3.3 | 0 | 2 | 6 | 2 | 10 |
| 65 | 96 | 98 | 103 | 94 | 95 | 97.2 | 3.6 | 2 | 5 | 9 | 1 | 17 |
| 66 | 95 | 99 | 95 | 99 | 97 | 97.0 | 2.0 | 4 | 4 | 4 | 2 | 14 |
| 67 | 95 | 97 | 102 | - | 96 | 98.2 | 3.1 | 2 | 5 | 1 | 5 | 13 |
| 68 | 97 | 97 | 105 | 94 | 99 | 98.4 | 4.1 | 0 | 8 | 11 | 5 | 24 |
| 69 | 94 | 97 | 95 | 95 | 97 | 95.6 | 1.3 | 3 | 2 | 0 | 2 | 7 |
| 70 | 99 | 98 | 97 | 93 | 95 | 96.4 | 2.4 | 1 | 1 | 4 | 2 | 8 |
| 71 | 95 | 97 | 95 | 97 | 95 | 95.8 | 1.1 | 2 | 2 | 2 | 2 | 8 |
| 72 | 97 | 95 | 98 | - | 101 | 98.4 | 2.6 | 2 | 3 | 3 | 0 | 8 |
| 73 | 94 | 90 | 97 | 96 | 97 | 94.8 | 2.9 | 4 | 7 | 1 | 1 | 13 |
| 74 | 94 | 92 | 97 | 98 | 93 | 94.8 | 2.6 | 2 | 5 | 1 | 5 | 13 |
| 75 | 96 | 99 | 92 | 98 | 95 | 96.0 | 2.7 | 3 | 7 | 6 | 3 | 19 |
| 76 | 95 | 95 | 101 | - | 94 | 97.6 | 4.1 | 0 | 6 | 2 | 9 | 17 |
| 77 | 96 | 99 | 99 | 93 | 103 | 98.0 | 3.7 | 3 | 0 | 6 | 10 | 19 |
| 78 | 92 | 98 | 98 | - | 101 | 97.8 | 3.5 | 6 | 0 | 2 | 1 | 9 |
| 79 | 98 | 101 | 97 | 91 | 97 | 96.8 | 3.6 | 3 | 4 | 6 | 6 | 19 |
| 80 | 94 | 101 | 96 | - | 95 | 97.4 | 3.4 | 7 | 5 | 5 | 6 | 23 |
| 81 | 100 | 95 | 95 | 99 | 103 | 98.4 | 3.4 | 5 | 0 | 4 | 4 | 13 |
| 82 | 96 | 93 | 101 | - | 100 | 98.8 | 4.3 | 3 | 8 | 3 | 4 | 18 |
| 83 | 95 | 95 | 99 | - | 97 | 97.4 | 2.6 | 0 | 4 | 2 | 4 | 10 |
| 84 | 95 | 93 | 89 | 99 | 97 | 94.6 | 3.8 | 2 | 4 | 10 | 2 | 18 |
| 85 | 96 | 102 | 101 | - | 94 | 98.8 | 3.6 | 6 | 1 | 0 | 7 | 14 |
| 86 | 97 | 100 | 96 | 93 | 96 | 96.4 | 2.5 | 3 | 4 | 3 | 3 | 13 |
| 87 | 99 | 102 | 96 | 99 | 95 | 98.2 | 2.8 | 3 | 6 | 3 | 4 | 16 |
| 88 | *104* | 95 | 95 | 98 | 101 | 98.6 | 3.9 | 9 | 0 | 3 | 3 | 15 |
| 89 | 93 | 98 | 102 | - | 96 | 98.0 | 3.7 | 5 | 4 | 1 | 5 | 15 |
| 90 | 100 | 97 | 99 | 97 | 102 | 99.0 | 2.1 | 3 | 2 | 2 | 5 | 12 |
| 91 | 102 | 96 | 98 | 97 | 94 | 97.4 | 3.0 | 6 | 2 | 1 | 3 | 12 |
| 92 | 93 | 96 | 100 | 93 | 95 | 95.4 | 2.9 | 3 | 4 | 7 | 2 | 16 |
| 93 | 98 | 98 | 97 | 96 | 101 | 98.0 | 1.9 | 0 | 1 | 1 | 5 | 7 |
| 94 | 101 | 103 | 96 | 95 | 100 | 99.0 | 3.4 | 2 | 7 | 1 | 5 | 15 |
| 95 | 94 | 97 | 99 | 94 | 95 | 95.8 | 2.2 | 3 | 2 | 5 | 1 | 11 |
| 96 | 99 | 102 | 99 | - | 102 | 101.2 | 2.2 | 3 | 3 | 5 | 2 | 13 |
| 97 | 95 | 96 | 98 | 99 | 100 | 97.6 | 2.1 | 1 | 2 | 1 | 1 | 5 |
| 98 | 95 | 91 | 96 | 96 | 99 | 95.4 | 2.9 | 4 | 5 | 0 | 3 | 12 |
| 99 | 95 | 96 | 98 | - | 93 | 96.6 | 3.0 | 1 | 2 | 3 | 8 | 14 |
| 100 | 101 | 97 | 94 | - | 96 | 97.6 | 2.9 | 4 | 3 | 6 | 4 | 17 |

*Fig. 4 (b)*

ASD/Sigma
Sum: 14.8
3.09 <--average of subgroup sigmas
4.77

| Correlat | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 0 | 4.65 | 4.54 | 4.63 | 4.59 | 4.9 | 4.93 | 4.88 | 4.69 | 4.78 | 4.87 | 4.81 | 4.8 | 4.89 | 4.8 | 4.71 | 4.8 | 4.92 | 4.7 | 4.6 | 4.61 |
| 0.00 | 4.69 | 4.66 | 4.65 | 4.69 | 4.57 | 4.68 | 4.59 | 4.62 | 4.48 | 4.64 | 4.7 | 4.71 | 4.84 | 4.68 | 4.94 | 4.95 | 4.84 | 4.75 | 4.9 | 4.65 |
| 0.01 | 4.59 | 4.66 | 4.53 | 4.68 | 4.64 | 4.56 | 4.44 | 4.45 | 4.6 | 4.58 | 4.65 | 4.52 | 4.62 | 4.55 | 4.68 | 4.67 | 4.44 | 4.71 | 4.81 | 4.59 |
| 0.02 | 4.49 | 4.51 | 4.55 | 4.71 | 4.6 | 4.39 | 4.62 | 4.54 | 4.58 | 4.41 | 4.45 | 4.56 | 4.4 | 4.48 | 4.54 | 4.41 | 4.7 | 4.49 | 4.55 | 4.76 |
| 0.04 | 4.48 | 4.45 | 4.44 | 4.53 | 4.73 | 4.31 | 4.51 | 4.41 | 4.27 | 4.66 | 4.4 | 4.62 | 4.52 | 4.5 | 4.42 | 4.64 | 4.39 | 4.46 | 4.56 | 4.42 |
| 0.06 | 4.27 | 4.29 | 4.46 | 4.49 | 4.57 | 4.39 | 4.31 | 4.62 | 4.46 | 4.25 | 4.21 | 4.43 | 4.19 | 4.42 | 4.49 | 4.31 | 4.42 | 4.6 | 4.17 | 4.42 |
| 0.09 | 4.29 | 4.3 | 4.33 | 4.36 | 3.99 | 4.54 | 4.46 | 4.35 | 4.4 | 4.22 | 4.36 | 4.14 | 4.38 | 4.43 | 4.24 | 4.2 | 4.15 | 4.33 | 4.51 | 4.63 |
| 0.12 | 4.07 | 4.15 | 4.42 | 4.11 | 4.19 | 4.23 | 4.29 | 4.09 | 4.28 | 4.3 | 4.28 | 4.11 | 4.14 | 4.37 | 4.37 | 4.26 | 4.46 | 4.04 | 4.47 | 4.17 |
| 0.16 | 4.38 | 4.11 | 4.19 | 4.18 | 4.36 | 4.12 | 4.31 | 4.14 | 4.17 | 4.19 | 4.32 | 4.23 | 4.22 | 4.18 | 4.15 | 4.2 | 3.93 | 4.14 | 4.19 | 4.16 |
| 0.2 | 4.24 | 4.01 | 3.97 | 4.15 | 4.23 | 4.07 | 3.91 | 4.21 | 3.98 | 4.16 | 4.07 | 4.06 | 4.14 | 3.8 | 3.99 | 4.03 | 4.07 | 3.83 | 4.01 | 4.04 |
| 0.25 | 4 | 4.05 | 3.75 | 4.07 | 4.01 | 3.78 | 4.06 | 3.89 | 4.08 | 4.05 | 4.13 | 3.99 | 4.09 | 4.04 | 3.87 | 4.06 | 3.85 | 4.05 | 4.18 | 3.97 |
| 0.3 | 3.84 | 3.69 | 3.93 | 4.02 | 3.93 | 4.02 | 3.74 | 3.81 | 3.85 | 3.78 | 3.84 | 3.75 | 3.83 | 4.21 | 3.96 | 3.83 | 3.89 | 4.0 | 4 | 3.77 |
| 0.36 | 3.86 | 3.79 | 3.53 | 3.77 | 3.9 | 3.9 | 3.77 | 3.83 | 3.84 | 3.96 | 3.88 | 3.68 | 3.83 | 3.89 | 3.75 | 3.73 | 3.89 | 3.76 | 3.77 | 3.97 |
| 0.42 | 3.7 | 3.75 | 3.55 | 3.56 | 3.89 | 3.78 | 3.68 | 3.65 | 3.63 | 3.84 | 3.71 | 3.64 | 3.53 | 3.58 | 3.73 | 3.6 | 3.64 | 4.04 | 3.67 | 3.64 |
| 0.49 | 3.36 | 3.81 | 3.55 | 3.49 | 3.49 | 3.85 | 3.31 | 3.42 | 3.55 | 3.48 | 3.31 | 3.43 | 3.46 | 3.54 | 3.66 | 3.71 | 3.44 | 3.47 | 3.31 | 3.47 |
| 0.56 | 3.38 | 3.32 | 3.14 | 3.4 | 3.3 | 3.43 | 3.32 | 3.29 | 3.34 | 3.34 | 3.42 | 3.39 | 3.43 | 3.26 | 3.46 | 3.4 | 3.14 | 3.32 | 3.3 | 3.46 |
| 0.64 | 3.01 | 3.15 | 2.98 | 3.24 | 2.84 | 3.07 | 3.14 | 3.15 | 3.08 | 3.38 | 3.03 | 3.07 | 3.1 | 3.12 | 3.41 | 2.97 | 3.21 | 3.28 | 3.39 | 3.18 |
| 0.66 | 2.8 | 2.94 | 3.05 | 2.99 | 2.91 | 3.03 | 2.91 | 3.05 | 3.28 | 3.23 | 3.04 | 3.24 | 3.32 | 3.07 | 3.01 | 3.26 | 2.99 | 3.14 | 3.25 | 3.06 |
| 0.67 | 3.06 | 2.97 | 3 | 2.89 | 3.12 | 3.15 | 2.56 | 3.07 | 2.88 | 3.14 | 3.27 | 3.1 | 2.8 | 2.93 | 3.05 | 2.99 | 2.85 | 2.86 | 3.11 | 3.04 |
| 0.69 | 2.7 | 3.08 | 2.9 | 2.74 | 2.92 | 2.78 | 3.09 | 2.93 | 3.03 | 2.87 | 2.96 | 2.82 | 2.77 | 2.89 | 2.83 | 2.83 | 2.71 | 3.08 | 2.77 | 2.78 |
| 0.71 | 2.86 | 2.61 | 2.86 | 3.25 | 2.65 | 2.71 | 2.97 | 2.79 | 2.86 | 2.6 | 2.86 | 2.88 | 2.78 | 2.77 | 2.9 | 2.75 | 2.82 | 2.91 | 2.92 | 2.76 |
| 0.72 | 2.82 | 2.7 | 2.86 | 2.67 | 2.72 | 2.81 | 2.97 | 2.64 | 2.72 | 2.7 | 2.68 | 2.63 | 2.74 | 2.81 | 2.62 | 2.73 | 2.58 | 2.85 | 2.8 | 2.78 |
| 0.74 | 2.54 | 2.54 | 2.64 | 2.68 | 2.77 | 2.79 | 2.67 | 2.73 | 2.56 | 2.65 | 2.63 | 2.62 | 2.57 | 2.59 | 2.85 | 2.87 | 2.86 | 2.74 | 2.76 | 2.76 |
| 0.76 | 2.73 | 2.57 | 2.66 | 2.61 | 2.67 | 2.51 | 2.53 | 2.63 | 2.4 | 2.63 | 2.48 | 2.49 | 2.67 | 2.63 | 2.62 | 2.52 | 2.5 | 2.48 | 2.38 | 2.68 |
| 0.77 | 2.52 | 2.47 | 2.36 | 2.52 | 2.57 | 2.59 | 2.58 | 2.26 | 2.46 | 2.33 | 2.44 | 2.53 | 2.38 | 2.65 | 2.58 | 2.54 | 2.53 | 2.5 | 2.6 | 2.33 |
| 0.79 | 2.3 | 2.54 | 2.37 | 2.37 | 2.31 | 2.49 | 2.24 | 2.35 | 2.37 | 2.22 | 2.8 | 2.38 | 2.4 | 2.36 | 2.23 | 2.21 | 2.24 | 2.28 | 2.44 | 2.28 |
| 0.81 | 2.3 | 2.34 | 2.16 | 2.14 | 2.23 | 2.3 | 2.4 | 2.27 | 2.33 | 2.46 | 2.2 | 2.41 | 2.13 | 2.2 | 2.47 | 2.29 | 2.15 | 2.44 | 2.35 | 2.33 |
| 0.83 | 2.45 | 2.25 | 2.32 | 2.15 | 2.2 | 2.06 | 2.25 | 2.13 | 2.32 | 2.35 | 2.16 | 2.35 | 2.26 | 2.29 | 2.17 | 2.15 | 2.35 | 2.08 | 2.36 | 2.25 |
| 0.85 | 1.97 | 2.04 | 2.06 | 2.12 | 2.03 | 2.02 | 2.23 | 2.23 | 2.12 | 2.02 | 2.29 | 2.14 | 2.04 | 2.06 | 2.1 | 2.11 | 2.41 | 2.08 | 2.22 | 2.07 |
| 0.86 | 2.01 | 1.99 | 2.31 | 2.08 | 2.03 | 2.36 | 2.18 | 2.07 | 1.99 | 1.98 | 1.97 | 1.99 | 1.99 | 2.08 | 2.14 | 1.98 | 2.01 | 1.83 | 1.94 | 2.01 |
| 0.88 | 1.83 | 1.83 | 1.83 | 1.83 | 2.01 | 2.24 | 2.24 | 2.24 | 1.83 | 2.12 | 2.24 | 2.08 | 2.01 | 1.94 | 2.24 | 2.08 | 0 | 2.12 | 2.77 | 2.24 |
| 0.9 | 2.24 | 1.83 | 1.83 | 1.83 | 1.83 | 0 | 1.83 | 2.24 | 2.08 | 1.83 | 1.83 | 0 | 2.01 | 0 | 2.24 | 1.83 | 0 | 1.83 | 0 | 1.94 |
| 0.92 | 0 | 0 | 0 | 0 | 0 | 0 | 0 | 0 | 0 | 0 | 2.24 | 0 | 0 | 0 | 0 | 2.24 | 0 | 0 | 0 | 0 |
| 0.94 | 0 | 0 | 0 | 0 | 0 | 0 | 0 | 0 | 0 | 0 | 0 | 0 | 0 | 0 | 0 | 0 | 0 | 0 | 0 | 0 |
| 0.96 | 0 | 0 | 0 | 0 | 0 | 0 | 0 | 0 | 0 | 0 | 0 | 0 | 0 | 0 | 0 | 0 | 0 | 0 | 0 | 0 |
| 0.98 | 0 | 0 | 0 | 0 | 0 | 0 | 0 | 0 | 0 | 0 | 0 | 0 | 0 | 0 | 0 | 0 | 0 | 0 | 0 | 0 |

*Fig. 4 (c)*

| Linear | Nonli | Two step | |
|---|---|---|---|
| 5.47 | 4.17 | 4.89 | |
| 5.28 | 4.35 | 4.79 | |
| 5.1 | 4.49 | 4.69 | |
| 4.91 | 4.6 | 4.58 | |
| 4.72 | 4.35 | 4.48 | |
| 4.53 | 4.7 | 4.38 | |
| 4.34 | 4.7 | 4.28 | |
| 4.15 | 4.66 | 4.18 | |
| 3.96 | 4.59 | 4.08 | |
| 3.77 | 4.48 | 3.97 | |
| 3.58 | 4.34 | 3.87 | |
| 3.39 | 4.16 | 3.77 | |
| 3.2 | 3.95 | 3.67 | |
| 3.02 | 3.7 | 3.57 | |
| 2.83 | 3.41 | 3.46 | |
| 2.64 | 3.09 | 3.36 | |
| 2.45 | 2.73 | 3.26 | |
| 2.41 | 2.66 | 3.24 | |
| 2.37 | 2.58 | 3.22 | <- |
| 2.33 | 2.5 | 3.2 | <- |
| 2.3 | 2.42 | 3.16 | |
| 2.26 | 2.34 | 2.97 | |
| 2.22 | 2.25 | 2.78 | |
| 2.18 | 2.17 | 2.59 | |
| 2.15 | 2.08 | 2.39 | |
| 2.11 | 2 | 2.2 | |
| 2.07 | 1.91 | 2.01 | |
| 2.03 | 1.82 | 1.82 | |
| 1.99 | 1.73 | 1.63 | |
| 1.96 | 1.63 | 1.43 | |
| 1.92 | 1.54 | 1.24 | |
| 1.88 | 1.44 | 1.05 | |
| 1.84 | 1.35 | 0.86 | |
| 1.8 | 1.25 | 0.67 | |
| 1.77 | 1.15 | 0.48 | |
| 1.73 | 1.05 | 0.28 | |

Regression Output:
Constant              5.474
Std Err of Y Est      0.74
R Squared             0.719
No. of Observation    36
Degrees of Freedc     34

X Coefficie  -3.782
Std Err of(  0.406

Regression Output:
Constant              4.171
Std Err of Y Est      0.53
R Squared             0.86
No. of Observation    36
Degrees of Freedc     33

X Coefficie  3.904  -7.131
Std Err of(  1.367   1.239

1  0 to 0.82 // graph to
2  0.83 ... graph from 0.

1 Regression output:
Constant              4.89
Std Err of Y Est      0.114
R Squared             0.961
No. of Observation    19
Degrees of Freedc     17

X Coofficie  -2.038
Std Err of(  0.099

2 Regression output:
Constant              19.29
Std Err of Y Est      0.461
R Squared             0.825
No. of Observation    17
Degrees of Freedo     15

X Coefricie  -19.19
Std Err of(  2.282

*Fig. 4 (d)*

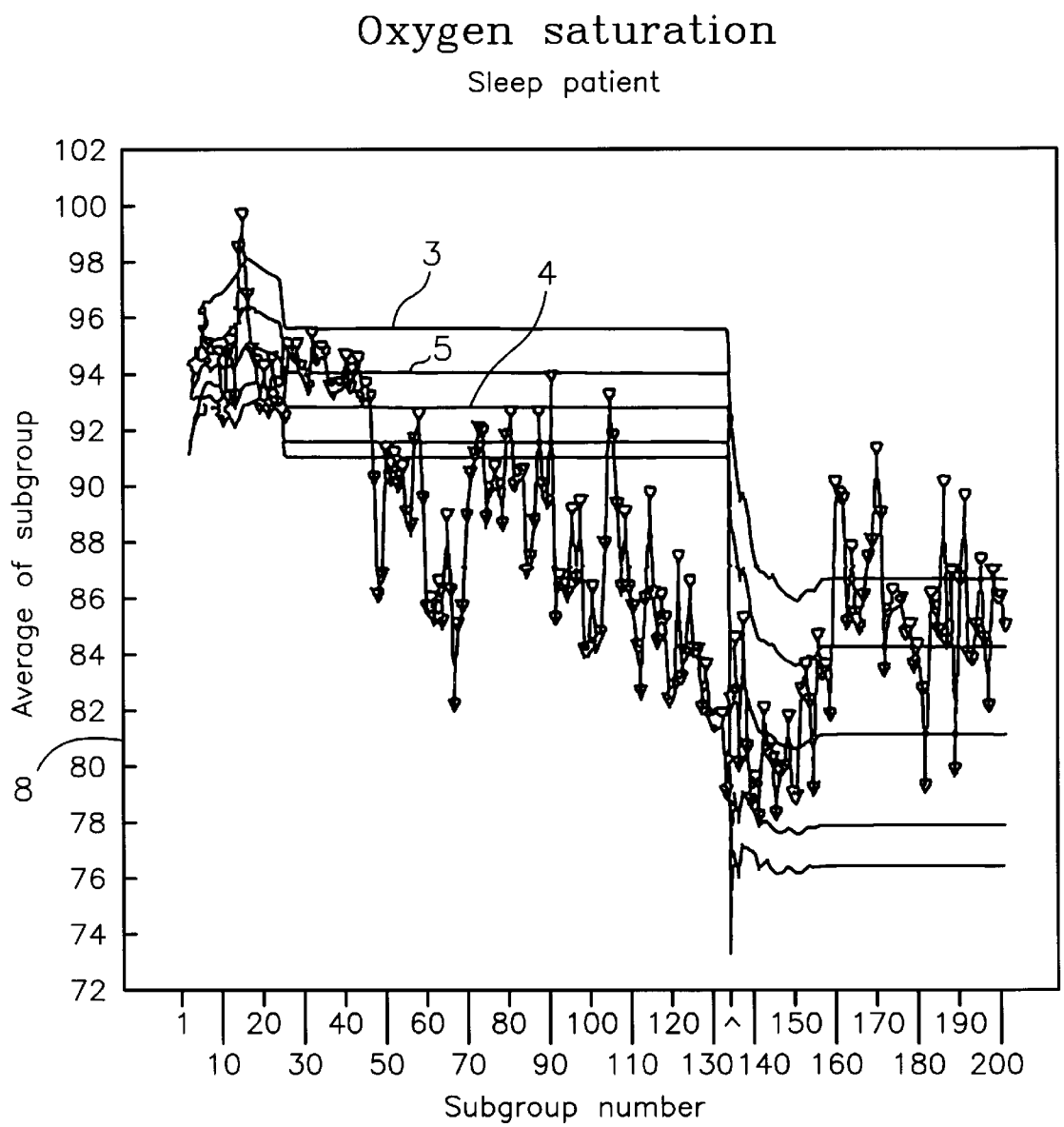
Fig. 5 (a) (i)

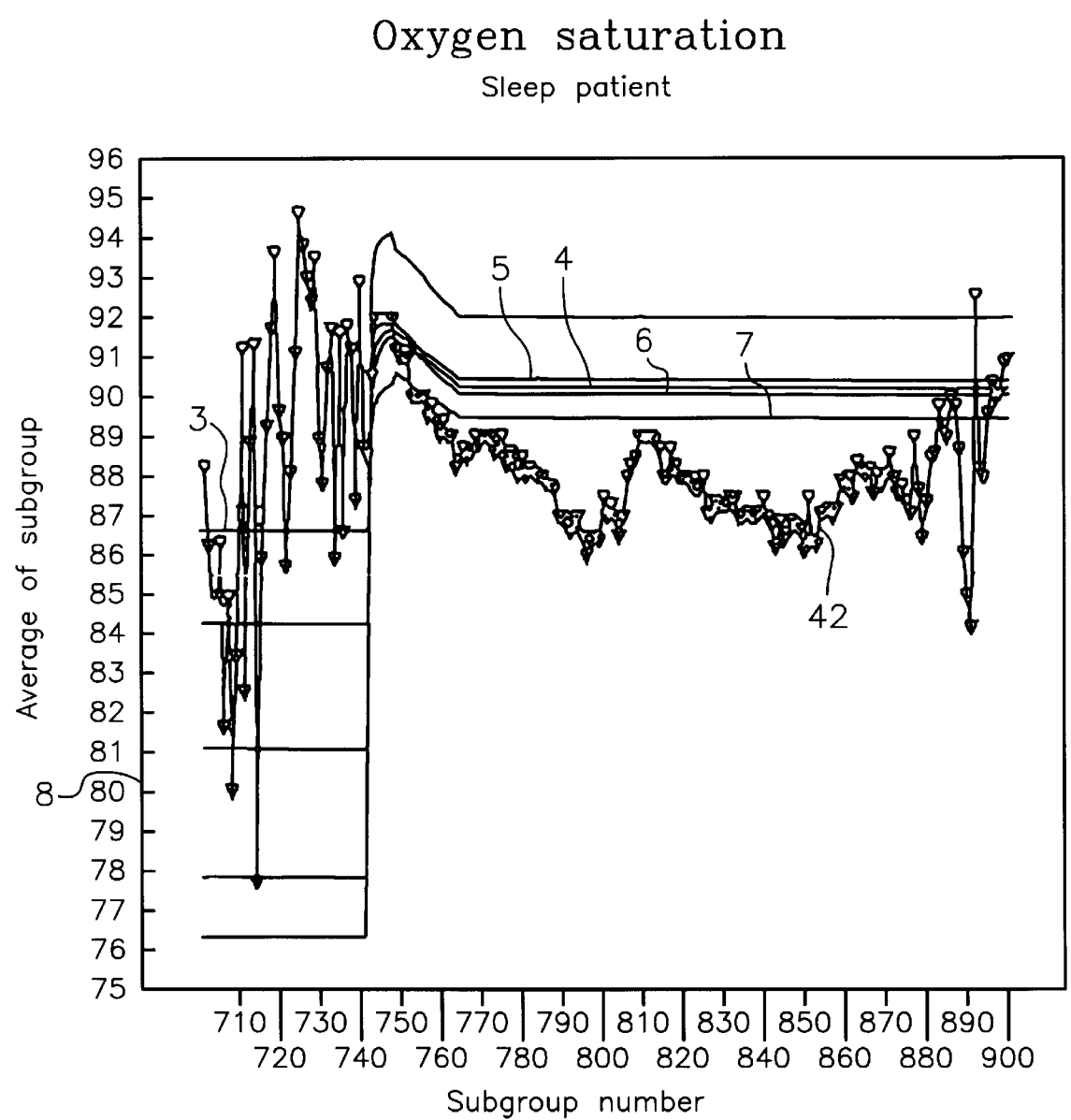
Fig. 5 (a) (ii)

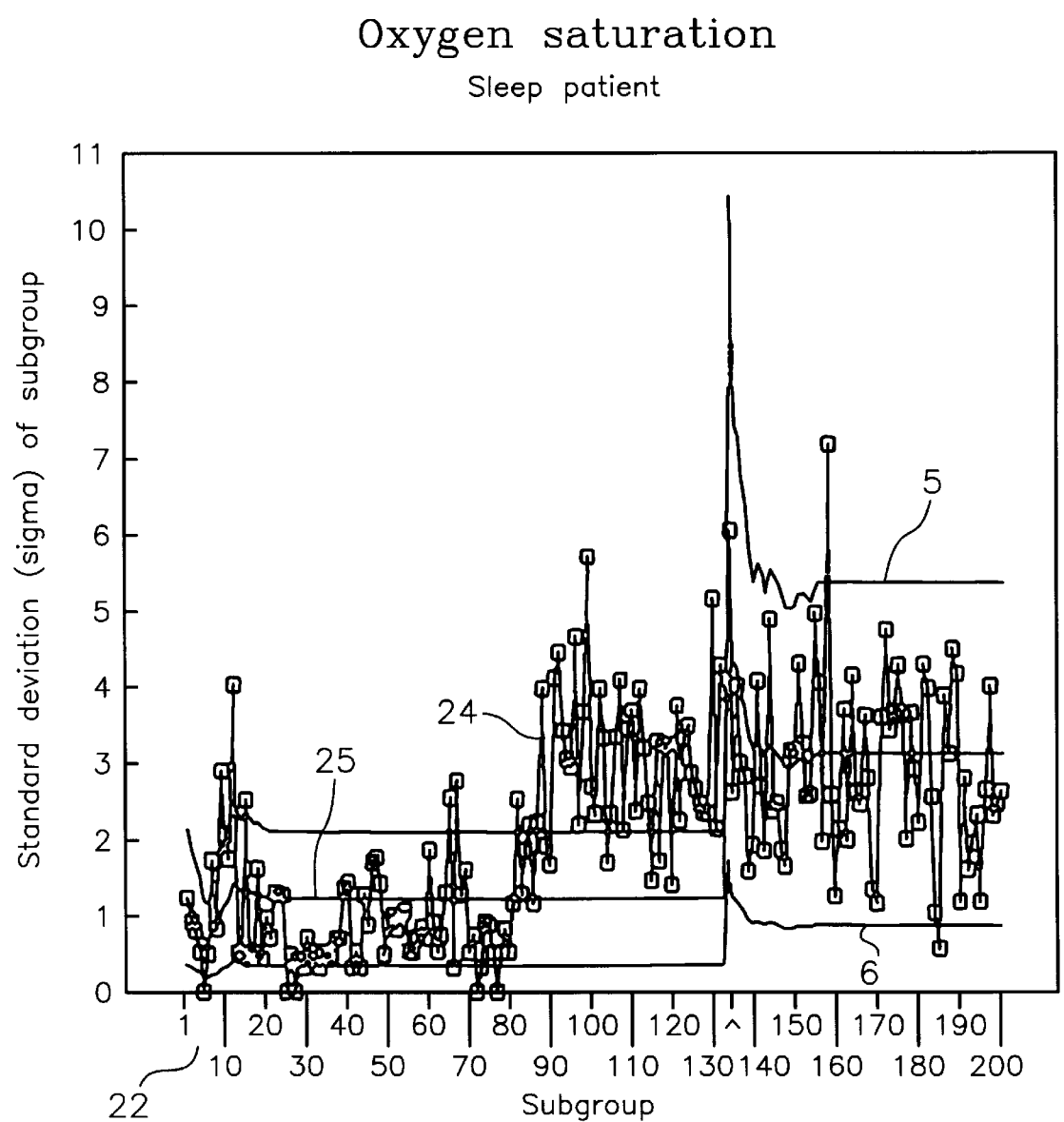
Fig. 5 (b) (i)

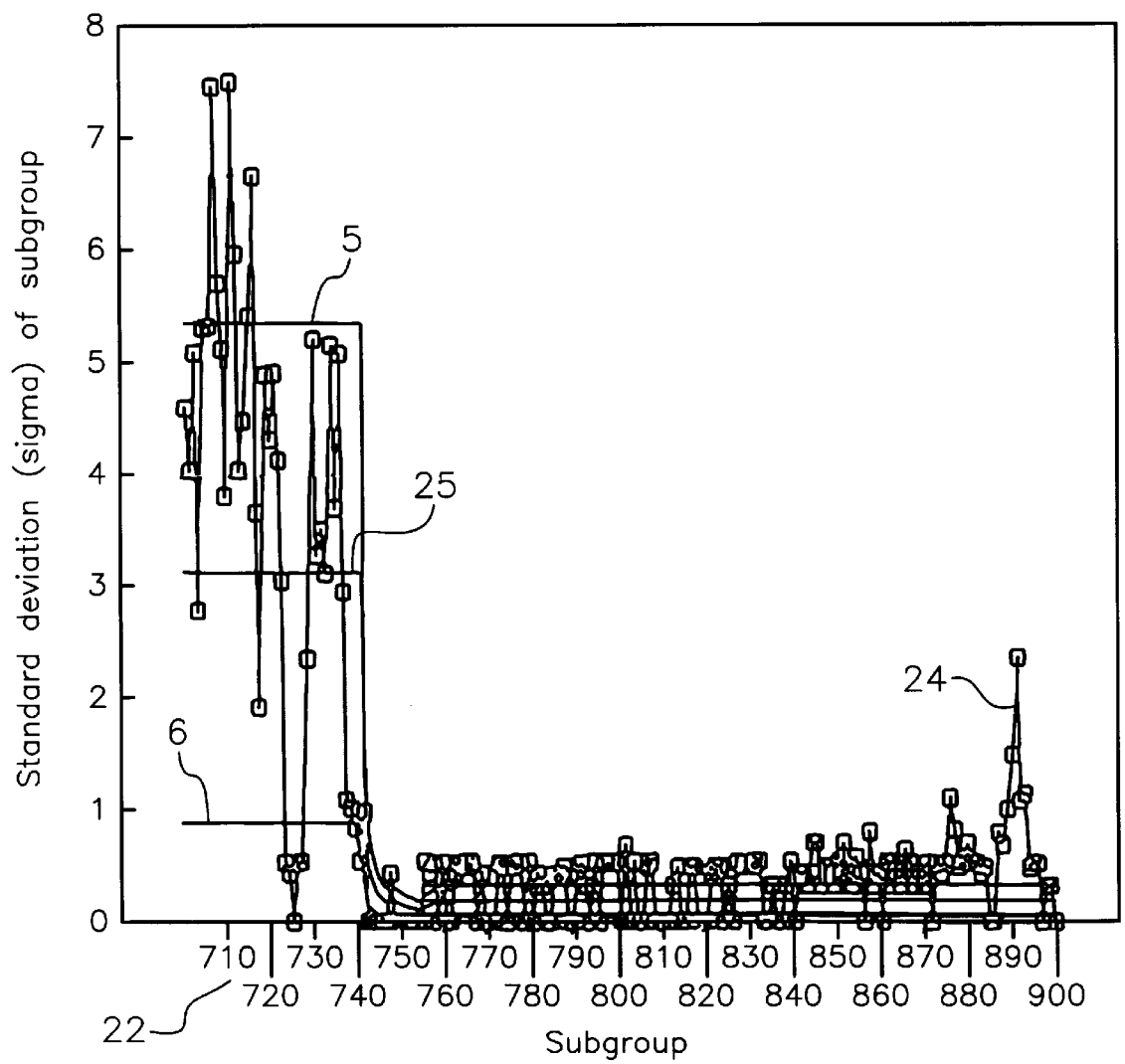
Fig. 5 (b) (ii)

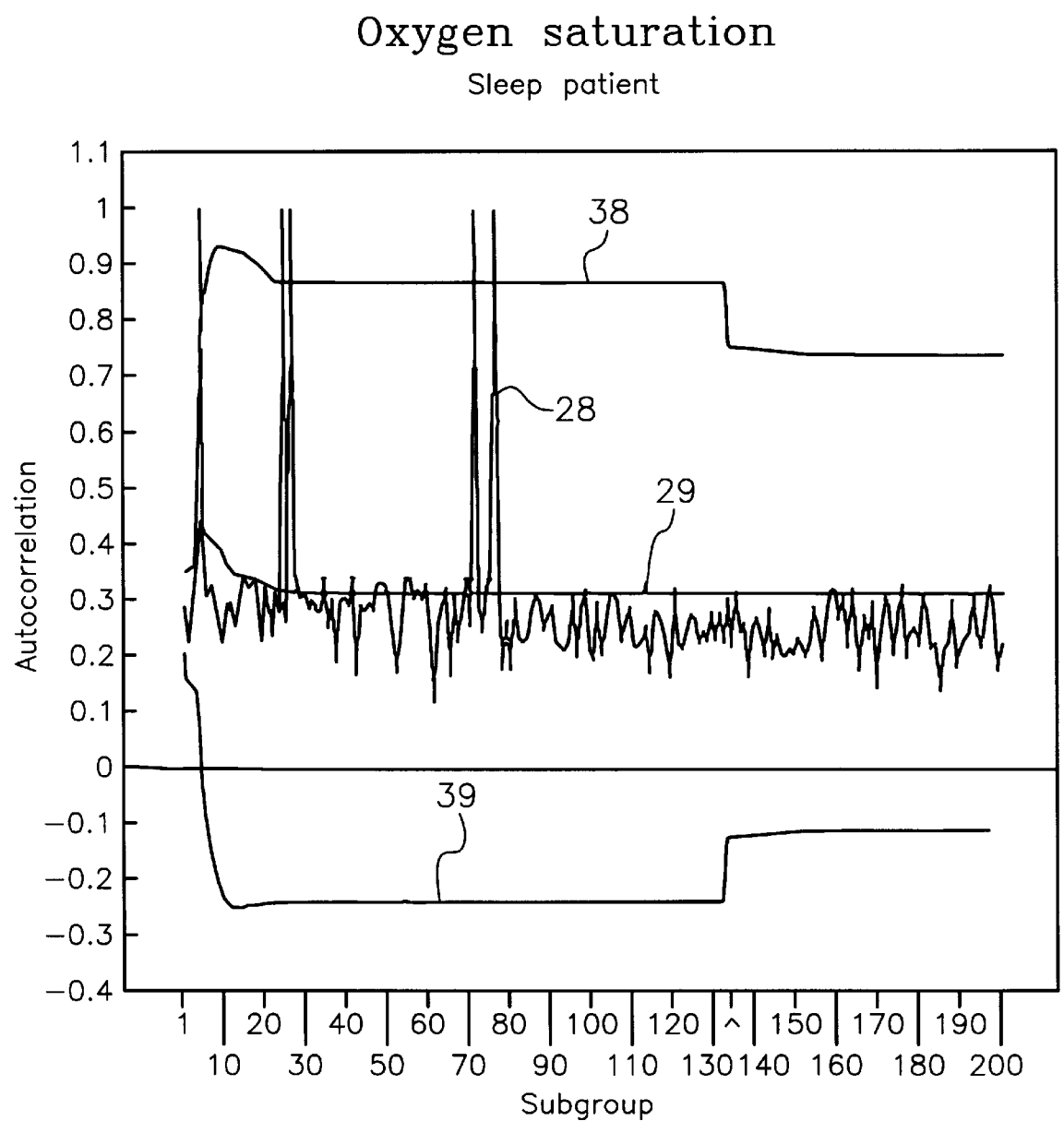
Fig. 5 (c) (i)

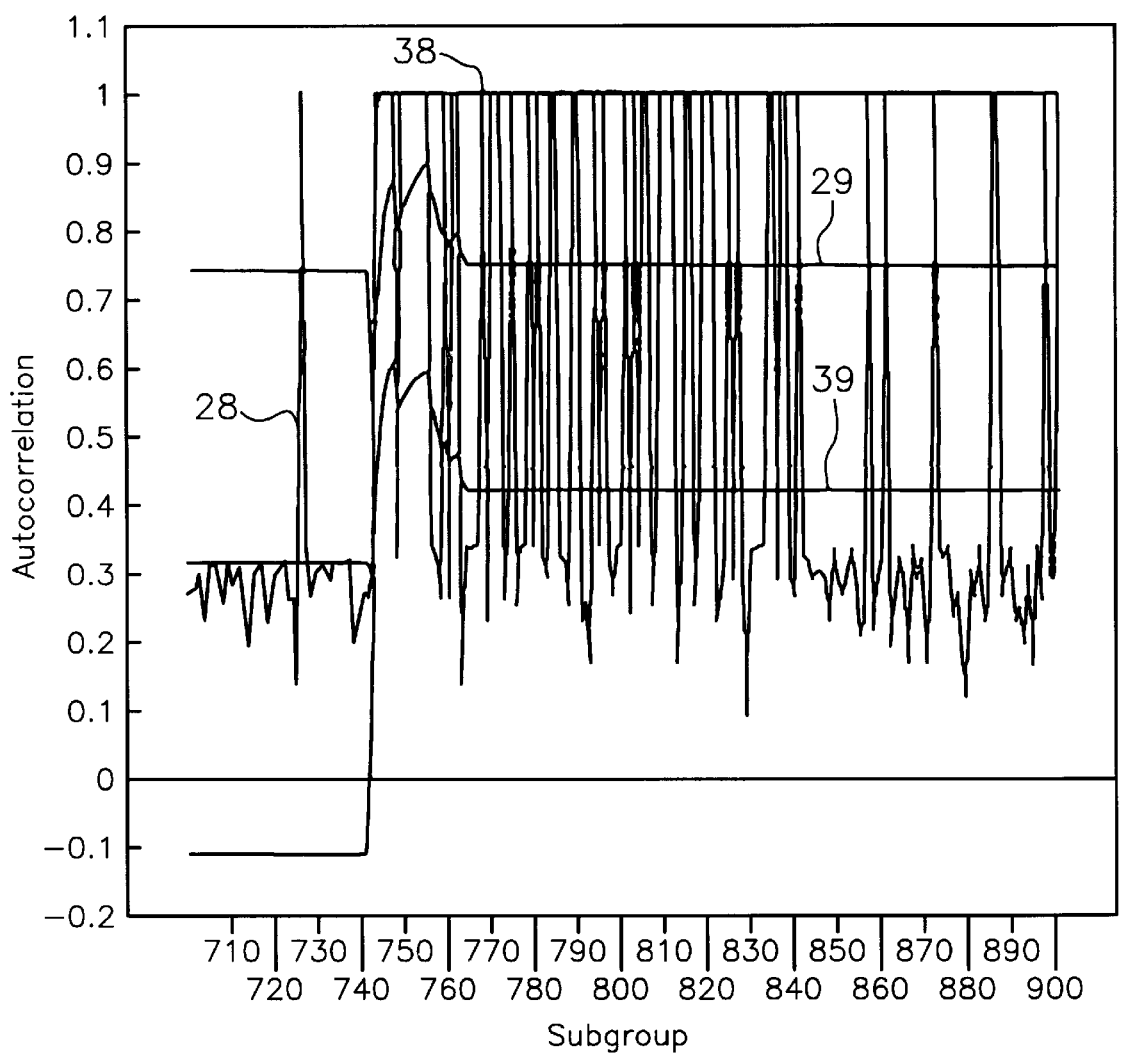
Fig. 5 (c) (ii)

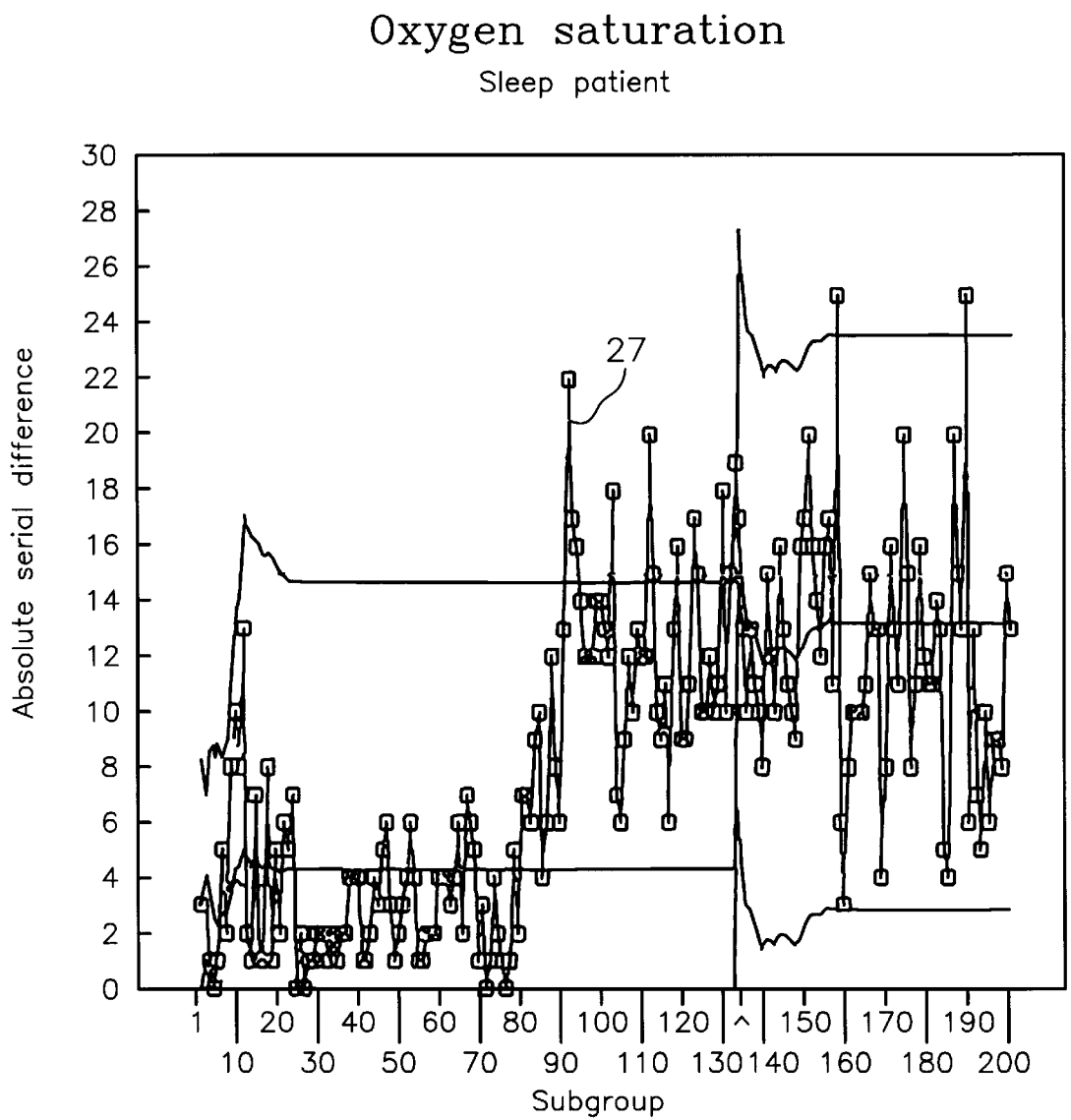
Fig. 5 (d) (i)

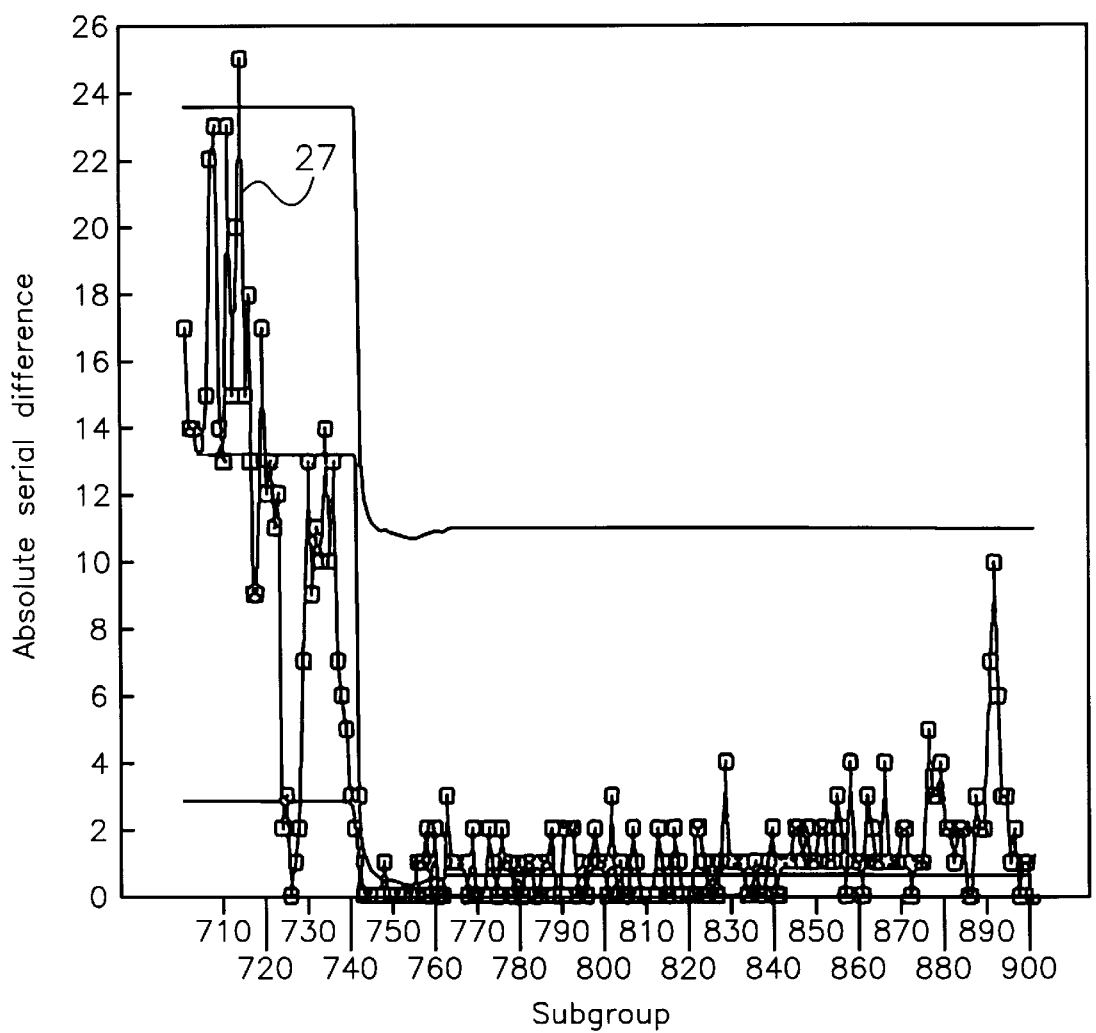
Fig. 5 (d) (ii)

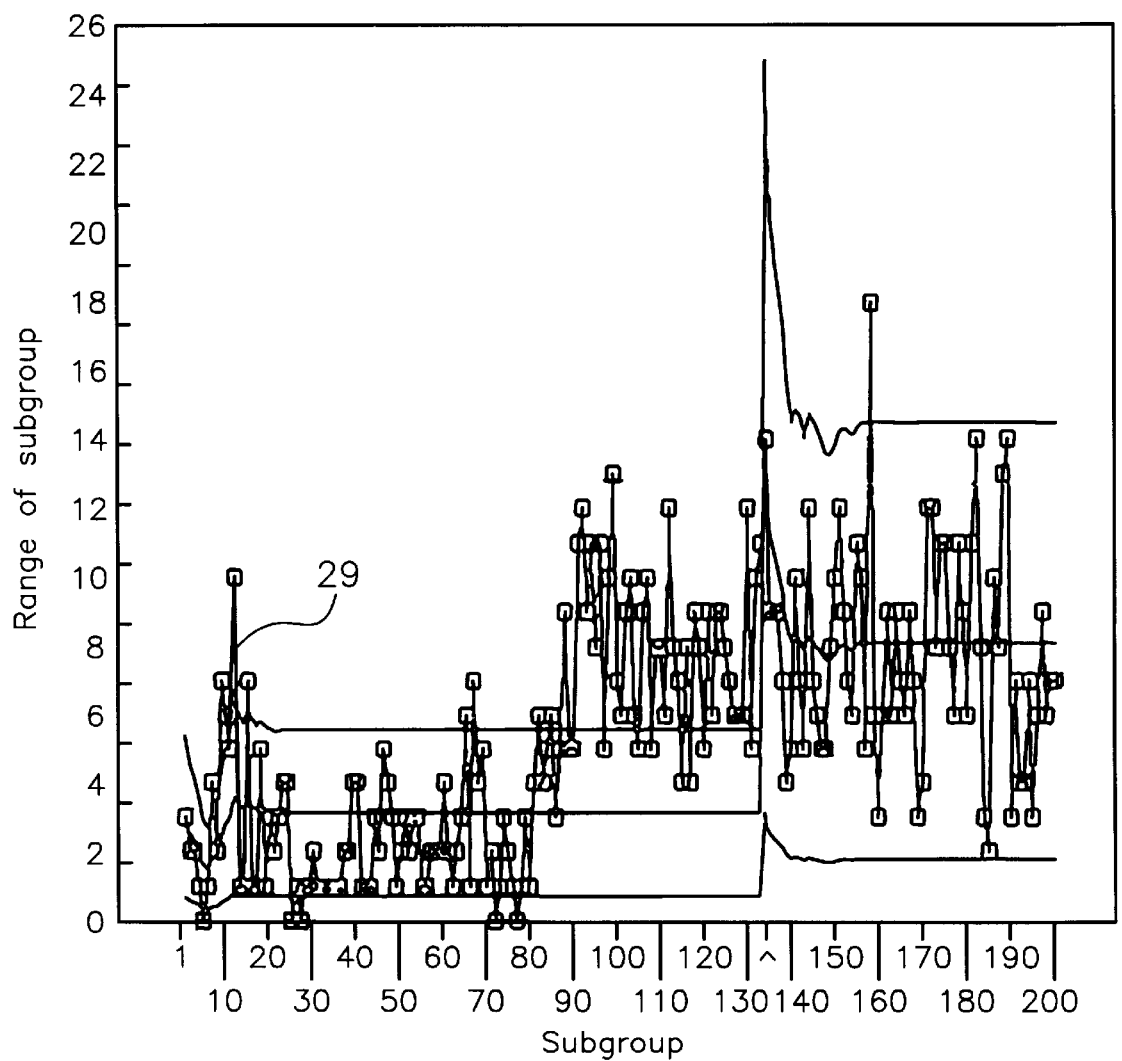
Fig. 5 (e) (i)

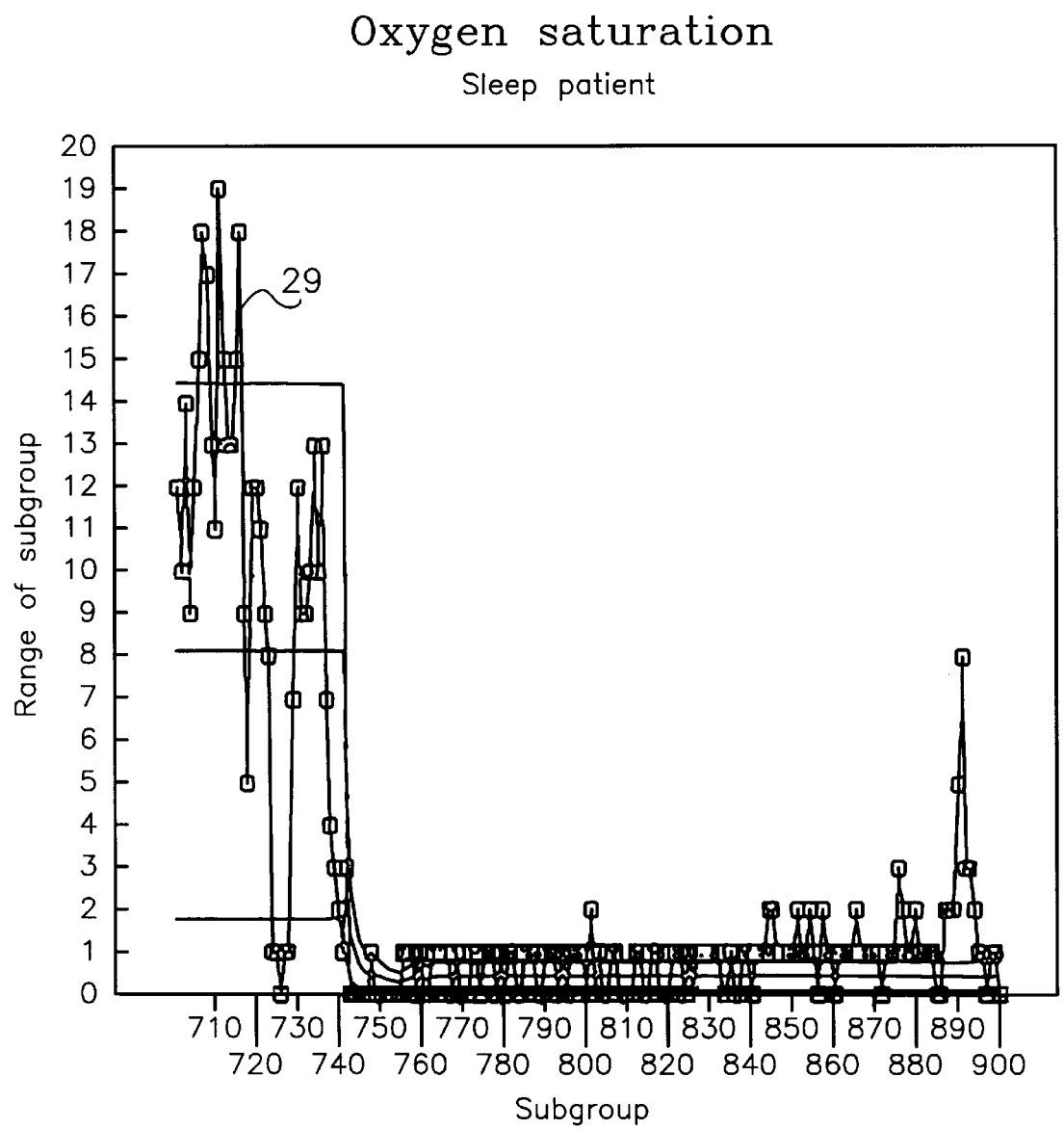
Fig. 5 (e) (ii)

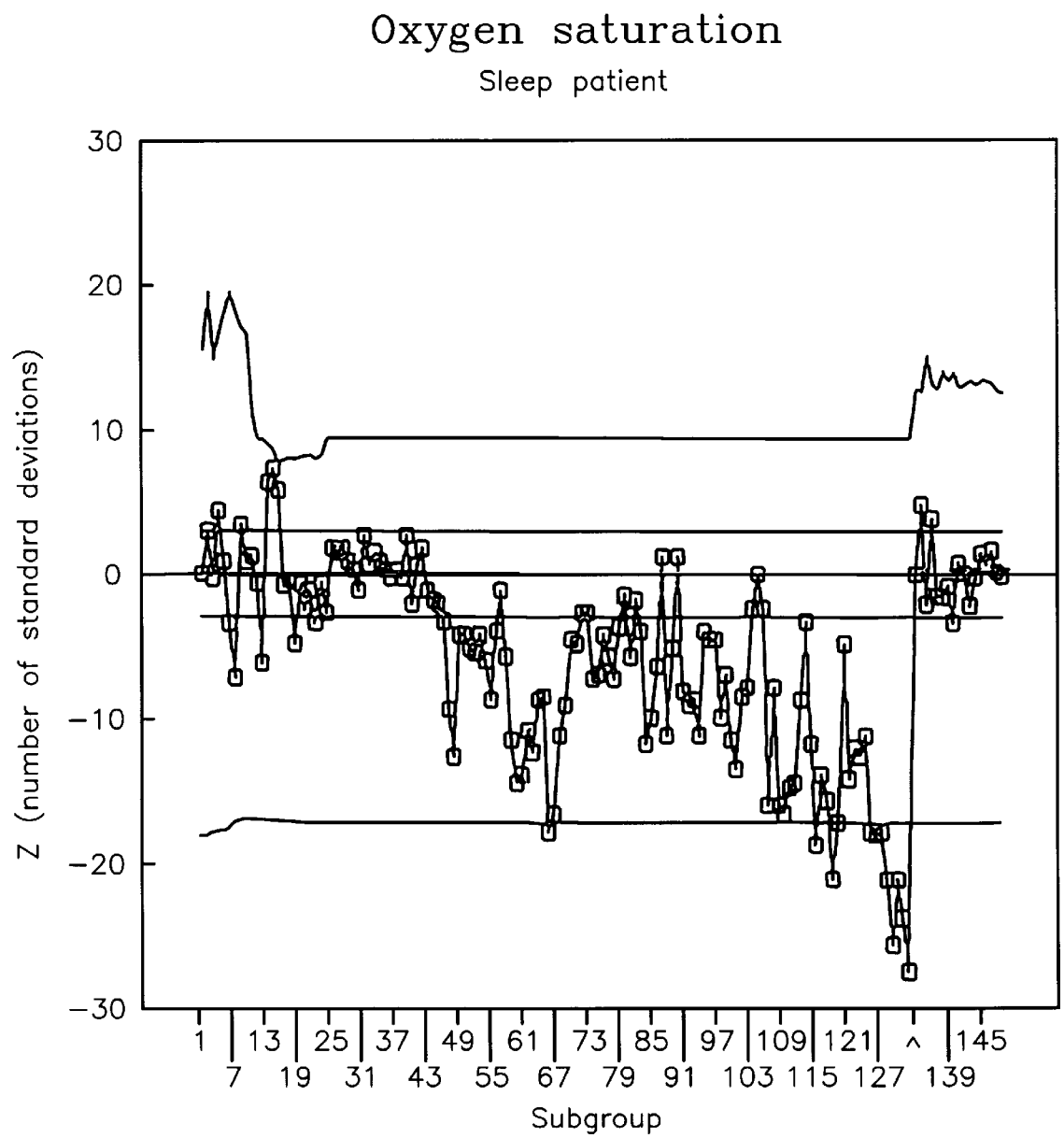
Fig. 5 (f) (i)

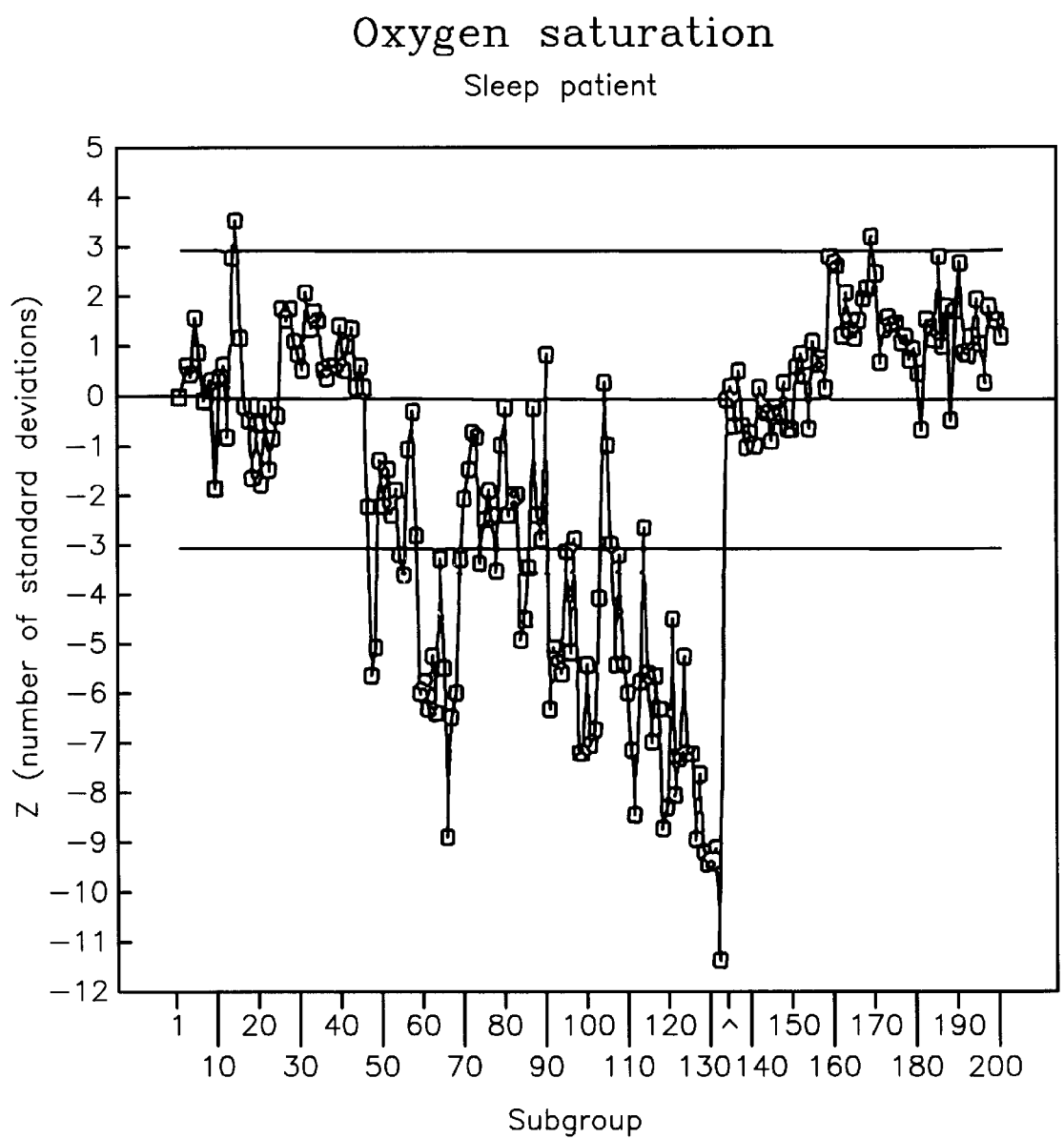
Fig. 5 (f) (ii)

| A-E Ratio | Autocorr |
|---|---|
| 2.78604 | 0.00 |
| 2.78865 | 0.05 |
| 2.71607 | 0.10 |
| 2.73766 | 0.15 |
| 2.67987 | 0.20 |
| 2.64077 | 0.25 |
| 2.63893 | 0.30 |
| 2.63149 | 0.35 |
| 2.60127 | 0.40 |
| 2.56403 | 0.45 |
| 2.-54034 | 0.50 |
| 2.51277 | 0.55 |
| 2.46353 | 0.60 |
| 2.42724 | 0.65 |
| 2.37831 | 0.70 |
| 2.30662 | 0.75 |
| 2.26711 | 0.80 |
| 2.20048 | 0.81 |
| 2.21216 | 0.82 |
| 2.17097 | 0.83 |
| 2.14929 | 0.84 |
| 2.10443. | 0.85 |
| 2.08942 | 0.86 |
| 2.08077 | 0.87 |
| 2.01100 | 0.88 |
| 2.02365 | 0.89 |
| 1.97168 | 0.90 |
| 1.95763 | 0.91 |
| 1.92855 | 0.92 |
| 1..80693 | 0.93 |
| 1.70763 | 0.94 |
| 1.04355 | 0.95 |
| 0.37947 | 0.96 |
| 0.00000 | 0.97 |
| 0.00000 | 0.98 |
| 0.00000 | 0.99 |

*Fig. 7*

MEDICAL DATA DISPLAY METHOD

PRIORITY APPLICATION

This is a continuation in part of application Ser. No. 08/519,508, filed Aug. 25, 1995, now abandoned which is a continuation in part of application Ser. No. 08/176,475, filed Jan. 3, 1994, now abandoned.

BACKGROUND OF INVENTION

This invention applies to measures of data in the medical environment. More specifically, the invention applies to determining measures of stability or consistence of serial data in numeric or graphical form for individual patients as part of the medical monitoring process.

PRIOR ART

The prior art shows a method of using quality control charts in order to evaluate clinical analysis data. The closes examples of statistical analysis in the medical environment includes: (1) Zimmerman. et al., U.S. Pat. No. 5,199,439; which details the use of Shewhart type process control charts for on-line medical monitor; (2) Bell. et al.; U.S. Pat. No. 3,322,954; which includes the diagnosis of statistically significant variations of radiation; (3) Hutchins; U.S. Pat. No. 4,583,524; which processes information for medical diagnosis or treatment; (4) Hrushesky; U.S. Pat. No. 4,519,395; which uses statistically analyzed mean and standard error in heart rate; (5) John; U.S. Pat. No. 4,545,388; shows the application of basic statistical computation of mean and variance for a self individual norm. None of these patents measure autocorrelation or address the issue of homeostasis in patient data.

U.S. Pat. No. 3,980,075 Sep. 14, 1976 Photoelectric Physiological Measuring Apparatus is an apparatus for measurement of data. This type of product could be used in conjunction with the control charts discussed.

Other art includes U.S. Pat. No. 5,564,433 issued to Thornton (which is not included as prior art since it was filed after the original patent application from which priority is sought); U.S. Pat. No. 4,844,086 issued to Duffy and U.S. Pat. No. 5,215,098 issued to Steinhaus, et al. In particular, these are relatively static measures of correlation. The present application is directed towards taking the data observed in patents, taking statitical measurements, inserting the statistical measurements into a control chart and modifying the limits according to correlation and running this continually against the data over a period of time. While the changes in correlation between any given data points is useful (used in the cited art), the present invention is more clearly seen as following data in statiscal formats (such as average data from a statistically significant subgroup of readings) against control charts with limits modified for correlation determined using models or actual patient data indicating a desired level of correlation. This compares with the art cited which makes a determination based on the photograph of correlation at one point in time. These patents look to a measure of correlation as an end. The present specification follows correlation over an extended period of time and uses the value of the correlation to better understand the values displayed over a period of time for the underlying data. Particularly, the data is better understood when the results are graphed within control charts modified to take into account the amount of correlation. That the value of the correlation at any point in time may be valuable in itself is secondary, particularly where correlation is varied intentionally over time as in, for example, anesthesia effected data. This is also why the present application suggests using control readings from a control group of patients in order to determine correlation while the prior art looks only at the patient's correlation.

None of these cited patents utilize consistency or autocorrelation in order to manipulate control chart data. The present invention could be used as an enhancement for analyzing the data generated by instrumentation used in the referenced patents if a sufficient amount of data was generated to generate control charts.

U.S. Pat. No. 4,519,395 May 28, 1985 discloses medical Instrument for noninvasive measurement of Cardiovascular characteristics and carries out a classic statistical analysis such as linear regression after collecting data. The specification does not perform an modification of Shewhart Process Control Chart or display statistics for autocorrelation and/or homeostasis. One difference between this prior art and the specification is to that the specification set forth below allows for improving monitoring data displayed in control charts.

U.S. Pat. No. 4,463,762 Aug. 7, 1984 Apparatus for Obtaining an Objective Determination of the Rate of Oxygen Utilization in Peripheral Tissue. This patent is for determining the rate of oxygen utilization in tissue. The specification does not perform an modification of Shewhart Process Control Chart or display statistics for homeostasis. One difference between this prior art and the specification is that the specification set forth below allows for improved monitoring.

U.S. Pat. No. 4,583,524 Apr. 22, 1986 Cardiopulmonary Resuscitation Prompting. This patent is for a portable self-powered electronic cardiopulmonary resuscitation unit. The patent includes some internal analysis, but does not include autocorrelation calculations nor real time graphing of output U.S. Pat. No. 4,545,388 Oct. 8, 1985 Self-Normed Brain State Monitoring. This patent works with a series of measurements from different parts of the brain. It seeks a base or normal level at an instant of time.

The specification set forth below is an enhancement for analyzing the data generated by an instrument such as is taught by the '524 patent. The specification below works with a series of measurements over time and an established base for a given time period to be used for comparison against the results generated by the current or future time periods. It establishes a base for both central tendency and variation. Hence, the specification below, does not cover the same material covered in the prior art specifications, but is an enhancement for analyzing the data generated by an instrument similar to these prior art patent specifications.

A current literature search indicates autocorrelation calculation methods are not real-time subgroup by subgroup. Relevant literature known to the inventor includes the following pertinent articles:

1. Brown, Lonnie D., Steven M. Zimmerman Ph.D., S. S. Brown, "Abstract-Medical Instrumentation+Quality Control=Earling Warning of Patient Instability", Association for the Advancement of Medical Instrumentation 25th Annual Meeting and Exposition 1990, p. 17.
2. Laffel, Glen, Robert Luttman, and Steven M. Zimmerman (1993), "Using Control Charts to Analyze Serial Patent-Related Data,", Submitted Sep. 26, 1993.
3. Al Pfadt and Donald J. Wheeler (1993), "Control Charts-Powerful Tools in a Clinical Setting," SPC Ink,
4. Zimmerman, Steven M., Robert N. Zimmerman, Lonnie D. Brown, and Shannon S. Brown, 91992) "Using Moving Average Process Control Charts in Biomedical Applications," Proceedings-Ninth International Conference of the Israel Society of Quality Assurance, 1992, Nov. 1992, 761–764.
5. Zimmerman, Steven M., Lonnie D. Brown, Shannon S. Brown, and Richard L. Goldhammer, M.D. (1990), "Quality Control Charts for Patient Data." The 18th International Conference of Israel Society for Quality Assurance Transactions Nov. 26–29, 1990 Jerusalem
6. Zimmerman, Steven M., Lonnie Brown, Shannon Brown, and Robert N. Zimmerman (1992) "Using the Theory of Runs in a Biomedical Application," 46th Annual Quality Control Congress Transactions May 18–20, p903–908.
7. Zimmerman, Steven M., Lonnie Brown, Shannon Brown, and Leroy Alexander (1990), "Human Body Function Control Charts for the Physician," 44th Annual Quality Congress Transactions May 14–16, p 408-.
8. Zimmerman, Steven M. and Robert N. Zimmerman (1992), SPC using Lotus 1-2-3. American Society of Quality Control and Quality Resources None of these prior art publications disclose the utilization of the process described below for manipulating control chart limits or data in medical monitoring.

GENERAL DISCUSSION OF THE INVENTION

Homeostasis is the maintenance of equilibrium, or constant condition, in a biological system. This is reflected in the constant heart rate, blood pressure and temperature found in patient monitoring. When the system maintaining equilibrium is disturbed, medical intervention is often necessary.

Correlation is the causal, complementary, parallel or reciprocal relationship between two measures of data. Autocorrelation or serial correlation is a subset of correlation which refers to the relationship of one data measure to a prior (or subsequent) data measure in a series of measurements. Correlation for plotted data may be determined by a formula. It may be interpreted generally as a measure of how closely the variables satisfy a linear relationship. Statisticians have defined other types of correlation in addition to the simple correlation between pairs of variables. Partial correlations are correlations between pairs of variables when the other variables are held constant. A multiple correlation is a correlation between one variable and a set of other variables.

Auto correlation may be more narrowly defined as the difference between a position and a prior position. The more related the two positions, the greater the auto correlation. Serial correlation is a subset of auto correlation where the difference is from one in a series of position from the preceeding position in the series.

One technique for investigating such a relation is called multiple regression analysis. The interpretation of correlation may reflect any of several different relationships between the measures of data. Depending upon the relationship viewed, the value or amount of correlation may vary.

Regression analysis is a statistical technique for investigating the relationship between a response variable (the dependent variable) and one or more explanatory, or independent, variables. Used to predict the behavior of the dependent variable from given values of the independent variables. It proceeds by (1) stating the form of a model linking the variables, (2) fitting this model to the data, (3) assessing whether the model fits well enough to be useful, and, if it does, (4) using the fitted model for prediction and other purposes.

If the dependent variable y is to be explained from a single independent variable x, the form of the model linking y and x might be assumed to be y=ax+b, where a and b are unspecified coefficients to be solved and the result is a linear (straight-line) relationship. A step function comprising multiple applications of this analysis to predict the behavior of dependant values is possible.

The data or control limits in a chart displaying data can be manipulated by factoring in a correcting factor. This factor, determined as a function of the value of correlation may be obtained as set forth above. Then, the correction is made by multiplying (or dividing) the factor times the data value or by the value representing the difference between the control limit and the average or the difference between the control limit and the data point. Since the factor may be determined ahead of time for various values of correlation found in the data to be plotted on the control chart, the correcting factors may be stored in a table matched with a correlation value and selected according to the match of the amount of correlation of the data to be corrected.

Autocorrelation, is the term used for measurement of data homeostasis, consistency, or similarity of patient data over time. Patient clinical data changes over time. What the specification focuses on is the change in the correlation between sets of data over time. A scale from 0 to 1 is used (effectively 0 percent to 100 percent correlation), although other measures could be used, such as 0 to 100 or 0 to 10. Measurement and calculations may be in backgroup where only the results are used.

Prior regression analysis includes a measure of homeostasis called autocorrelation. Normally, the data are collected and then regression, analysis of variance, or some other method is applied after the fact. This analysis is not used for patient data in the prior art.

Other limitations of the prior art in this area includes: (1) the failure to utilize autocorrelation as a measure of homeostasis; (2) the failure to utilize homeostasis to interpret medical data and particularly relative to administration of treatment to the patient; (3) the failure to recognize the importance of homeostasis relative to adjusting the controls on support systems and the administration of treatment. (4) Failure to recognize the importance of measuring and analysis the serial difference in data and, fundamental to this patent (5) the failure to adjust limits for control charts, such as the sigma limits in x-bar control charts, in real time, variable to the changing data, based on the correlation of the data. This is particularly true in medicine where the physician is intentionally make drastic changes in the physical condition of the patient and requires that the patient be maintained within certain ranges during this time period to avoid catastrophic consequences.

Hence, it is the purpose of this invention to to adjust limits for control charts, such as the sigma limits in x-bar control charts, in real time, variable to the changing data, based on the correlation of the data in a new and unobvious manner. It is a further purpose to manipulate existing patient specific data in order to better control the condition of the patient as the patient moves through changes brought about by the changing medical condition of the patient. It is a further purpose of this invention to maintain control limits for medical data within a useful range over time.

GENERAL DISCUSSION OF INVENTION

The invention discloses a method of using existing hardware to monitor patient specific data using a numeric or graphical format reflecting the condition of a monitored individual utilizing patient monitoring devices communicating between the patient monitoring device and computer devices or including a computer device internal to the monitor.

The primary reason for this innovation is to adjust limits for control charts, such as the sigma limits in x-bar control charts, in real time, variable to the changing data, based on the correlation of the medical, patient specific data. This is particularly true in medicine where the physician is intentionally make drastic changes in the physical condition of the patient and requires that the patient be maintained within certain ranges during this time period to avoid catastrophic consequences.

Because only a limited amount of the data are available and because any given point was not particularly significant, it was determined that x-bar (average) and sigma (standard deviation) control limits of the type set out in the Zimmerman patent cited above could be improved by utilizing autocorrelation, varied over real time, as a measure of consistency of data to vary the control limits with a moving limit.

Two general areas where this invention yields useful results are:

(1) Determining autocorrelation for statistically significant subgroups and utilizing the autocorrelation in order to forecast changes in the patients condition; and (2) Application of the autocorrelation statistic to modify data or to modify control limits in charts where data is displayed. In some instances, this means bringing the control limits back to where they would have been if the data was statistically independent.

One example of this process can be described generally as:

(1) communicating with a medical monitor (internal or external to the medical monitor);

(2) recording the data on some computer type media or paper;

(3) Selecting the specific data associated with a given quality characteristic at a specific time such as oxygen saturation from the data stream (The data would be in the format of x1, x2, x3, etc);

(4) grouping the data into statistically significant subgroups (The data would be in groups, e.g. x1–x10 in group a, x11–x20 in group b, ect);

(5) determining control chart statistics for the data (usually the average of each subgroup and sigma (standard deviation) for each subgroup);

(6) Determining a first and second measure of variation or homeostasis for a range of the data (In the preferred embodiment, the first twenty three data points are used as the come. Hence, the measures of variation used are for the first subgroup, the first two subgroups, the first three, the first four, and so on until 23 data blocks or subgroups are established to give a baseline).

(7) determining a factor to be used in concert with a ratio of the first and second measure of variation to be used to modify the control chart limits;

(8) modifying the control chart limits using the ratio determined in step 9;

(9) dynamically or statically displaying control chart statistics against the modified control chart limits;

(10) Alerting the user to variations in the control chart data outside of the prescribed limits;

(11) modifying the control chart limits based on the homeostasis method described in steps 1–8, for statistically significant variations of the control data where, for example, a predetermined number of points plotted fall outside of the set limits;

(12) maintaining a database of the results so that the data may be played back dynamically, printed on paper, or transferred to other programs for additional analysis including the occurances and extent of variation in the control chart limits.

The type of statistics displayed could include Shewhart type process control charts, or other process control charts such as the cumulative sum charts, exponential weighted moving average charts, grand mean moving average charts, or continuous hypothesis testing process control charts.

This type of process could include the use of the unadjusted charts along side of the adjusted charts so that information not related to autocorrelation could also be interpreted.

In one embodiment the charts may show medical conditions as recorded by the provider with control chart data. Because the provider's notes may not pick up the same conditions as quickly as the chart or because the providers notes may pick up on conditions that are not reflected in the charts the records will be taken largely from the provider's notes and inserted at the time that the provider's notes are taken in order to correlate the readings with provider's interpretations.

The provider may be forewarned about certain conditions arising by virtue of a comparison the information recorded with subsequent data samples giving the same or similar results.

The significance of data on patients with highly autocorrelated data as well as for patients who are not highly autocorrelated is compared for significance and treatment. Because autocorrelation is an indirect measure of homeostasis, it i s a measure of health.

Patient data which is highly autocorrelated is data not changing significantly between readings. Uncorrelated patient data will have readings which vary significantly between consecutive readings.

Determining the amount of correlation between sequential data samples (homeostasis) shows the significance where there is a relatively low amount of autocorrelation, a high autocorrelation and the transition period between high and low states.

Differences in correlation can reflect how and when a person's condition is going to change. An extremely high state of correlation can be expected when an event occurs and the readings are consistently very far out of their normal readings.

The opposite may occur. Where a person is undergoing preparation for surgery. Some conditions may be brought to a highly stabilized condition and at that point in time the auto correlation may be very high. Each data point would be very similar to other data.

When the surgery begins a shock is administered to the body. The autocorrelation drops very low as the body vital sign becomes more variable and then may resume a new state of high autocorrelation.

The transition period may be the indication of the on set of a distress state. Where patient treatment returns autocorrelation to a high state, the speed with which this happens may indicate a mechanism for controlling the patient and treatment of the patient.

Control charts monitoring patients may have control limits modified based on the amount of correlation in order to take into account the fact that many of the readings will be statistical aberrations as opposed to meaningful alarm events.

Homeostasis may have different significance when it occurs at different times in the healing or medication process. Homeostasis is generally understood in the art as a relatively stable state of equilibrium or a tendency toward such a state between different but interdependent elements or groups of elements of an organism or group. This equilibrium may occur at acceptable levels and unacceptable levels from the view point of the patient and healthcare provider. The equilibrium varies with the presence of life support assistance, patient medical condition and medication.

For most bodily functions, a low degree of autocorrelation is normal and therefore specific data points vary greatly and may fall outside sigma limits for upper and lower control limits in control charts. If a person's condition is going to change fairly rapidly, autocorrelation (or serial correlation - the correlation of successive data points) may become even lower. An extremely high state of correlation can also be expected when an event occurs such that all the readings are very far out of their normal readings. For example, death results in a heart rate (or lack of rate) which is consistent from reading to reading.

Identifying high autocorrelation false reports based on the wild fluctuations of data within control charts allow the user to modify the limits on data in order to take into account the fact that many of the readings will be statistical aberrations as to opposed to meaningful alarm events. When in homeostasis, the body has some unique behavior characteristics, which may be calculated using custom methods. Different homeostasis conditions or events may occur as the body passes through various aspects of the healing cycle.

One purpose of this invention is to provide the physician a measure of homeostasis, so that clinical judgements may be made. When in homeostasis, the body has some unique behavior characteristics, which may be calculated.

Another purpose of the invention is to apply a measure of the body's current homeostasis state to the clinical decision. If the body is in steady state, a treatment change is just as likely to change the state of the body as to change the level of performance of the body within a given state.

Another purpose of the homeostasis statistic is as an indicator for the need for improved measurement devices.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

FIGS. 2(a)–2(b) show actual patient data from prenatal heart monitory used to generate the charts shown in FIG. 3.

FIGS. 4(a)–4(d) show exemplary data used to generate the several charts shown in FIG. 5.

FIGS. 5(a)(i) and 5(a)(ii) show plots of the average subgroup verses the sub-group number showing normal control limits and adjusted upper and lower control limits.

FIGS. 5(b)(i) shows the standard deviation or sigma plotted using unadjusted control limits.

Paragraph FIG. 5(b)(ii) shows the same data shown in FIG. 5(b)(i) at a later point in time.

FIG. 5(c)(i) shows a linear determination of theta where the AE ratio is determined by using the serial difference correlation statistic divided by the average of sigma for the average for all the sub-groups.

FIG. 5(c)(ii) shows the same data as shown in 5(c)(i) at a later point in time and in particular it shows how the average can be changed for the autocorrelation in a sudden drop.

FIG. 5(d)(i) shows the graphing of the absolute serial difference correlation statistic as against the subgroups with upper and lower control limits.

FIG. 5(d)(ii) shows the same data as shown in 5(d)(i) when the correlation becomes high at a later point in time.

FIG. 5(e)(i) shows the range of sub-group correlations statistic.

FIG. 5(e)(ii) shows the range correlation statistic when data becomes highly correlated.

FIGS. 5(f)(i) and 5(f)(ii) show the standard deviations statistic graph.

Figure 6:
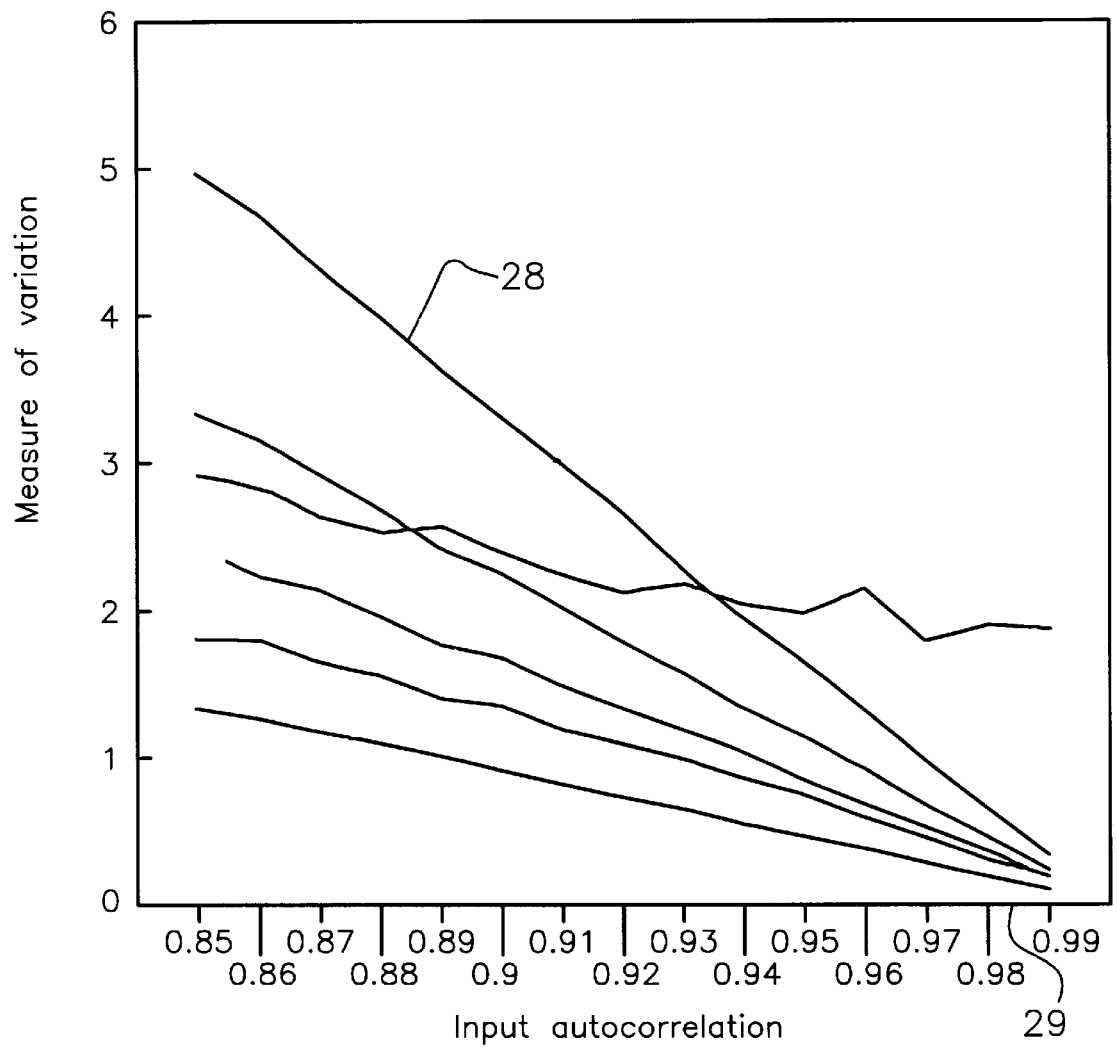

FIG. 6 shows graphically comparisons of different measures of autocorrelation between 0.85 and 0.99.

FIG. 7 is an example of a table showing autocorrelation correction factors next to values for autocorrelation.

Figure 8:
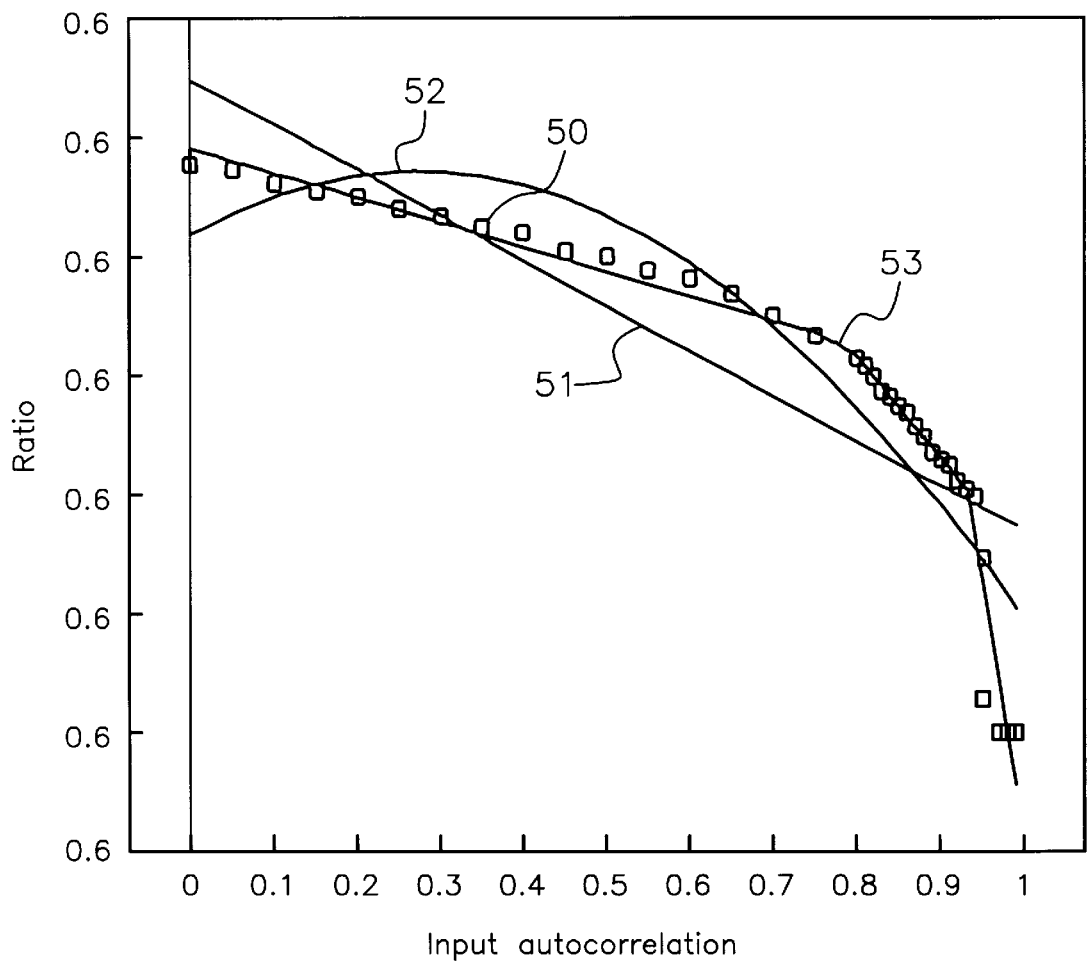

FIG. 8 shows linear and non linear plotting of regression analysis for subgroups of size 3,5,10 and 20.

DETAILED DISCUSSION OF THE PREFERRED EMBODIMENT(S)

The invention is generally described by the following process steps:

(1) communicating with a medical monitor (internal or external to the medical monitor);

(2) recording the data on some computer type media or paper;

(3) Selecting the specific data associated with a given quality characteristic at a specific time such as oxygen saturation from the data stream (The data would be in the format of x1, x2, x3, etc);

(4) grouping the data into statistically significant subgroups (The data would be in groups, e.g. x1–x10 in group a, x11–x20 in group b, ect);

(5) determining control chart statistics for the data (usually the average of each subgroup and sigma (standard deviation) for each subgroup);

(6) Determining a first and second measure of variation or homeostasis (a first and second correlation value) for a range of the data (In the preferred embodiment, the first twenty three data points are used as the come. Hence, the measures of variation used are for the first subgroup, the first two subgroups, the first three, the first four, and so on until 23 data blocks or subgroups are established to give a baseline).

(7) determining a ratio of the first and second measure of variation to arrive at a value of theta;

(8) determining a factor to be used in concert with theta, the ratio of the first and second measure of variation, to be used to modify the control chart limits;

(9) modifying the control chart limits using the ratio determined in step 9;

(10) dynamically or statically displaying control chart statistics against the modified control chart limits;

(11) Alerting the user to variations in the control chart data outside of the prescribed limits;

(12) modifying the control chart limits based on the homeostasis method described in steps 1–9, for statistically significant variations of the control data where, for example, a predetermined number of points plotted fall outside of the set limits; and

(13) maintaining a database of the results so that the data may be played back dynamically, printed on paper, or transferred to other programs for additional analysis including the occurances and extent of variation in the control chart limits.

The type of statistics displayed could include Shewhart type process control charts, or other process control charts such as the cumulative sum charts, exponential weighted moving average charts, grand mean moving average charts, or continuous hypothesis testing process control charts.

This type of process could include the use of the unadjusted charts along side of the adjusted a-charts so that information not related to autocorrelation could also be interpreted.

Steps 6–9 above and vary from what was disclosed in Zimmerman, et al., U.S. Pat. No. 5,199,439. Tracking correlation has been found to be useful in monitoring patient data where changes in correlation are significant. In addition, the control chart data abnormalities becomes more accurate when the limits are adjusted for the correlation present in the patient data. These are the primary area of discussion below.

Figure 1:
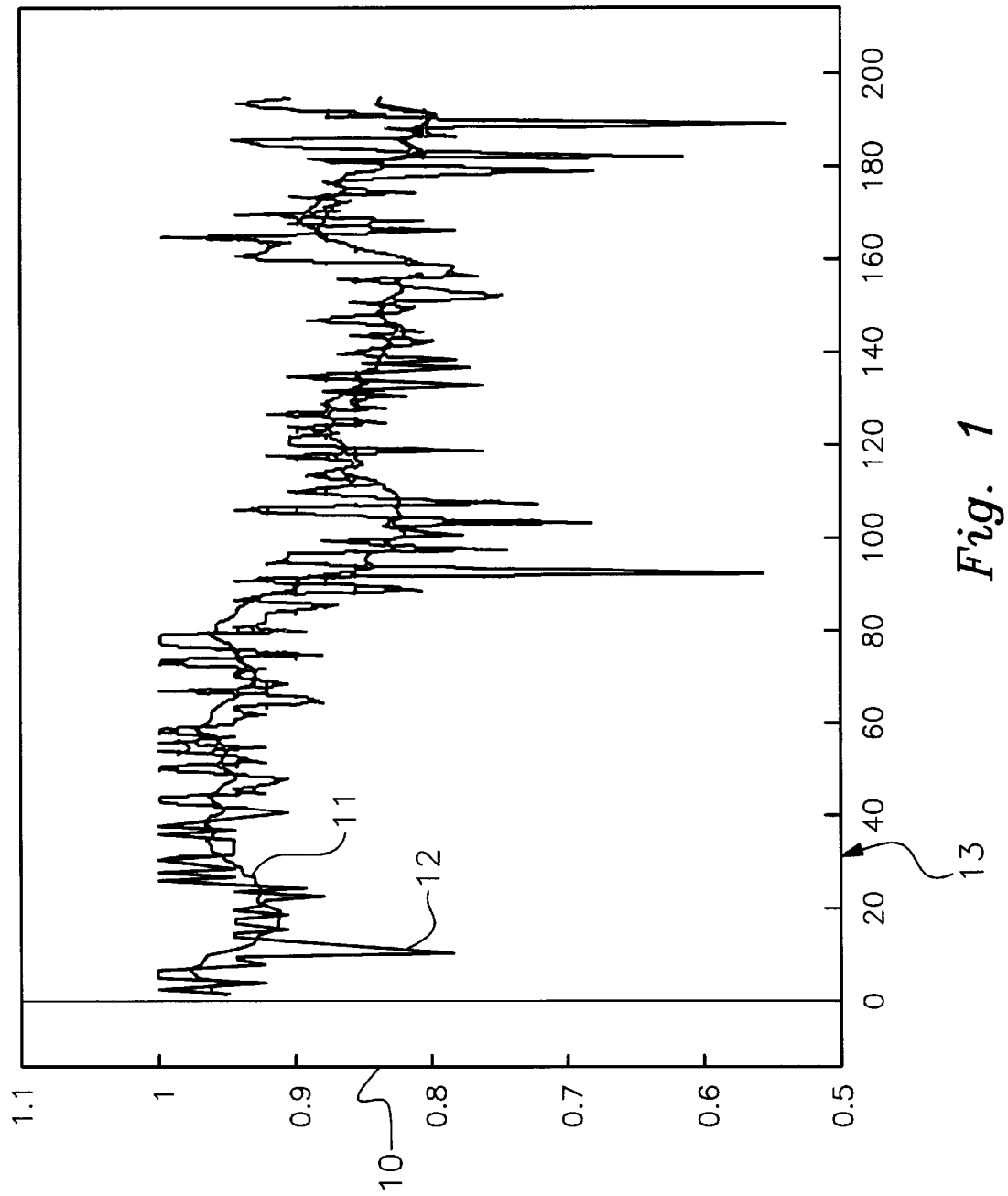
FIG. 1 is a graphical representation of a chart measuring autocorrelation using oxygen saturation on a scale from 0 to 1. Zero indicates completely uncorrelated data and 1 indicates 100 percent correlated data.

FIG. 1 shows a control chart measuring autocorrelation (homeostasis) 12 and average autocorrelation for patient oxygen saturation data on a scale from zero to one. No data points fall below zero-point-five. It should be noted that in the art a variety of scales may be used. This scale (zero to one) is used for purposes of the calculations described below. The graph is the correlation scale 10 against the subgroup scale 13 (in this case approximately 200 subgroups were used). This is generated using steps 1–7 above and generates a ratio which is plotted on FIG. 1.

As can be seen the amount of inconsistency (lack of correlation) is great in all of the data analyzed. That is, on a scale of 0 (completely correlated data, one subgroup being equal to the next) to 1 (completely uncorrelated data where one subgroup is different from the preceding subgroup); the data remains above 0.5 or 50% uncorrelated.

This measure of autocorrelation having an average shown in FIG. 1 is a measure referred to herein as Theta and is determined as set forth in more detail below.

Since autocorrelation as used herein is the measure of how one set of data (first in time) has changed relative to another set of data (second in time), the chart illustrates a patient's homeostasis.

FIGS. 5($a$)(i) and 5($a$)(ii) illustrates a Shewhart process control chart for subgroup averages. The top line is the adjusted upper control limit 3 for a process average 4 (here defined as an average of the averages) adjusted using autocorrelation data such as that shown in FIG. 1 to create the homeostasis control limits or adjusted upper control limit 3. The formula for making this is in more detail below. In this example, using theta as determined, the control limits are chaged. The same process is used for the lower control limit to arrive at a more realistic adjusted lower control limit 7. The chart shown is the average of subgroup scale against subgroup number 13. In this case, the correction factor used is 1/(1-theta) multiplied by the distance between average and unadjusted upper control limits 5. (This plot is generated in step 12).

Note how at approximately 135 the data becomes less correlated and thus the control limits 3 and 7 move out. Depending on the patient data in question, this now obvious change becomes important. For example, here, the oxygen saturation varies wildly (comparatively speaking) at points after 135. Conversly, FIG. 5($a$)(ii) shows the same type of data shown in FIG. 5($a$)(i) at a later point in time when the data becomes highly correlated at 740. While the data continues to fall outside of the control limits, which here cover data before the correlation occurred, the data has become more stable, the oxygen saturation is more stable and the control limits 3 and 7, being closer together, reflect this. This same change is reflected in FIG. 5($b$)(i) and ($b$)(ii) for standard deviation data.

In this case the A-E ratio (step 7) used was (abs serial diff)/(avg (sigma))=ratio. The correcting factor used is discussed in the process set forth in more detail below for linear step functions.

The value of Theta may come from a table of stored values for theta. Alternatively, it may be obtained according to the following process steps:

1. Collecting Data: Control Data are collected in the subgroups having a subgroup number on size of interest (3, 5, 10 and 20 are examples of subgroup sizes).

2. Recording the data with an assoicated factor of time;

3. Selecting the data. Another way of viewing this is to view it as normalizing Data: The next step is to make the data correspond to the normalized data, if necessary. For example, if the instrumentation used to collect patient data delivers data truncated to the nearest whole number, the next step is to truncate the control data to nearest whole number. This varies according to the format of the medical data as received. Another example would be where the medical device delivers data with two decimal points where the normal data would be truncated to the nearest two decimal points.

4. Grouping the data into statistically significant subgroups;

5. Determining control chart statistics for subgroups of the normalized data. In the preferred embodiments, the average and standard deviation is determined for the normalized data in subgroups;

6. Grouping Control Data according to autocorrelation: The data collected are grouped according to the amount of Autocorrelation. For purposes of this grouping, autocorrelation is then varied in increments (e.g 0–5, 5.1–10, 10.1–15, etc). Data used are autocorrelated in some readings and uncorrelated in other readings. Correlation is determined by measuring a correlation statistic described in more detail below, here using a number between 0 and 99. Control data used may be generated to fit the increment of autocorrelation or may be actual patient data having different degrees of correlation, or may be a hybrid of patient data and generated data. This grouping may be the identical grouping used in step 4 and is preferably the same. Alternatively, it may be vary using control data or by selecting different size subgroups. Several subgroups of size n (for example 3, 5, 10 or 20) are generated for serial readings from the collected data.

7. Determining a first and second autocorrelation statistic for the subgroups: An autocorrelation statistic, for example from the list of correlation statistics below, is then determined. For example, an average is made of the serial difference for each subgroup. In a subgroup of 5, for example, you would have 4 serial differences to average or sum.

FIG. 6 shows graphically comparisons of different measures of autocorrelation between 0.85 and 0.99. These include measures of autocorrelation. FIG. 6 shows different statistics graphed according to the amounts of correlation.

8. Determining a ratio of autocorrelation statistics: An optional step forward to give better results is to determine a ratio of correlation statistics for the data. For example, serial variation to total variation is then used to make the 'autocorrelation estimate ratio' (Hereinafter referred to as the A–E ratio). The A–E ratio is the statistic used to estimate the measure of autocorrelation. One example from the seven correlation statistics given below uses the absolute serial difference statistic 1 divided by statistic 6 average sigma. The method for calculating the numerator statistic or denominator statistic may vary from this list of correlation statistics without leaving the inventive concept embodied herein. For example, the sigma statistic may be used alone in place of the A–E ratio. In the preferred embodiment, the top number (numerator) is a statistic from the group shown below for serial variation; and he bottom number (denominator) is a different statistic also form the group shown below for total variation. Usually, the numerator would be a serial statistic and the denominator would be an absolute statistic (standard deviation).

Usually, several values of this ratio would be calculated and then the average ratio for multiple grouped data would be used. For example, the first subgroup and the second subgroup could be used to obtain an average of two until the third subgroup was generated, then the average would be the average of the three. The preferred embodiment uses at least 20 values to obtain an average value for this ratio. : An optional step would involve generation or collection of several groups of data. An average of the A–E ratio is then determined for each value of autocorrelation using steps 1–7 on each of the several data groups.

9. Determining an auto correcting factor: The main method used herein is an analysis of fitting a line to the results determined by steps 1–8. Alternatively the following two methods are available:

9($a$): Graphical Analysis: The A–E ratio (or averaged A–E ratio) is graphed against corresponding incremental values of autocorrelation (e.g. the Average A–E ratio for autocorrelation between 10 and 15 would be graphed between autocorrelation points 10 and 15.

9($b$). Standard least squares regression analysis as shown in FIGS. 8($a$) through 8($d$) (sum of least squares, linear and non-linear analysis) may be used to fit the average A–E ratio to input autocorrelation (the several different values of autocorrelation) to a specific formula which formula approximates the line formed by graphing the average A–E ratio to input auto correlation. This formula may be a first, second or third degree polynomial (e.g. First degree, Ax+51; second degree polynomial $ax^2+bx+52$; or a third degree polynomial $ax^3+bx^2+cx+d$) or it may be a step function as shown in FIGS. 8($a$) through 8($d$) [e.g. starting with a first degree polynomial and then switching to a second first degree polynomial or a second first degree polynomial] or a geometrical function (sin, cosine, etc) depending on the results of the graphing. The general formula is [(A–E ratio-factor 1)/factor 2].

In this case the formula determined for stepwise linear regression analysis 53 was, for subgroup size 3 (FIG. 8($a$)); subgroup size 5 (FIG. 8($b$)); subgroup size 10 (FIG. 8($c$)); subgroup size 20 (FIG. 8($d$)); utilizing truncated data.

|  | Input Correlation | Formula |
|---|---|---|
| FIG. 8(a) | 0 to 0.75 | 2.8166–0.6185X |
|  | 0.75 to 0.92 | 4.4713–2.7675X |
|  | 0.92 to 0.99 | 41.264–42.347X |
| FIG. 8(b) | 0 to 0.82 | 4.8903–2.0376X |
|  | 0.82 to 0.92 | 10.0354–8.588X |
|  | 0.92 to 0.99 | 40.771–41.31X |
| FIG. 8(c) | 0 to 0.80 | 10.674–5.7526X |
|  | 0.80 to 0.95 | 25.643–25.007X |
|  | 0.95 to 0.99 | 40.417–41.183X |
| FIG. 8(d) | 0 to 0.80 | 21.7245–13.565X only 2 step needed |
|  | 0.80 to 0.99 | 54.5395–55.585X |

Where X is the value of the A–E ratios.

As can be seen FIGS. 8($a$)–8($c$) have three steps and FIG. 8($d$) required only one step in the regression analysis.

10. Displaying the results Using the correlation factor determined in step the data, particularly the control limits may be manipulated.

11. Alerting the user to variation outside the modified limits. Determining when to manipulate data: One example shown here is to use autocorrelation to send an alarm and modify the control limits when there are six consecutive points outside of the normal control limits. FIG. 5($b$)(i) for example shows the limits adjusted at subgroup 134. A visual alert is given merely by the different limits.

12. Modifying the control chart limits. The steps 1–10 may be repeated as necessary to modify the control chart limits as conditions (and the amount of correlation) change.

13. Collecting patient data (as compared to control data).

14. Normalizing Data: The next step is to make the data correspond to the normalized data, if necessary. For example, if the instrumentation used to collect patient data delivers data truncated to the nearest whole number, the next step is to truncate normal data or generated truncation to nearest whole number. This varies according to the format of the medical data as received. Another example would be where the medical device delivers data with two decimal points where the normal data would be truncated to the nearest two decimal points.

15. Determining statistics for subgroups of the normalized data: An average and standard deviation is determined for the normalized data.

16. Manipulating data using theta: Theta is then used to vary the control limits. In this case the method used for varying the control limits is as follows: x=average-lower control limit. X times 1/(1-theta) yields the new control limits. The exact formula to vary the control limits can be varied according to the amount of adjustment desired (e.g. ½ of the A–E ratio may be used as opposed to the entire A–E ratio).

The formulas vary. Final formulas are a function of the exact statistics used and the nature of the data generated. The statistics are sensitive to all aspects of the data generation process, including but not limited to:

(1) truncation (round-off) of clinical data to whole numbers
(2) combination of small sigma with high autocorrelation
(3) overall variation measure (sigma, range, average of subgroup sigmas)
(4) serial variation measure (absolute serial difference, serial difference)

An example of truncation of data can be shown with Oxygen saturation data. This measure is 89 or 90, but it is never 89.5. One of the consequences of using truncated data is that the total variation may become zero at autocorrelation rates as low as 0.65 when sigma is small relative to the mean. For autocorrelated values greater than 0.96 using three digit data and an estimated standard deviation of approximately 3 percent it is common to obtain zero measures of overall variation with truncated data. With real number data, the total variation only becomes zero when the autocorrelation approaches 1. With small sigma and high autocorrelation, estimates of autocorrelation greater than one may occur.

The concept of total variation is simple. When searching for a statistic to measure the characteristic, things become complex. In a similar manner measuring serial variation requires a decision.

Figure 3:
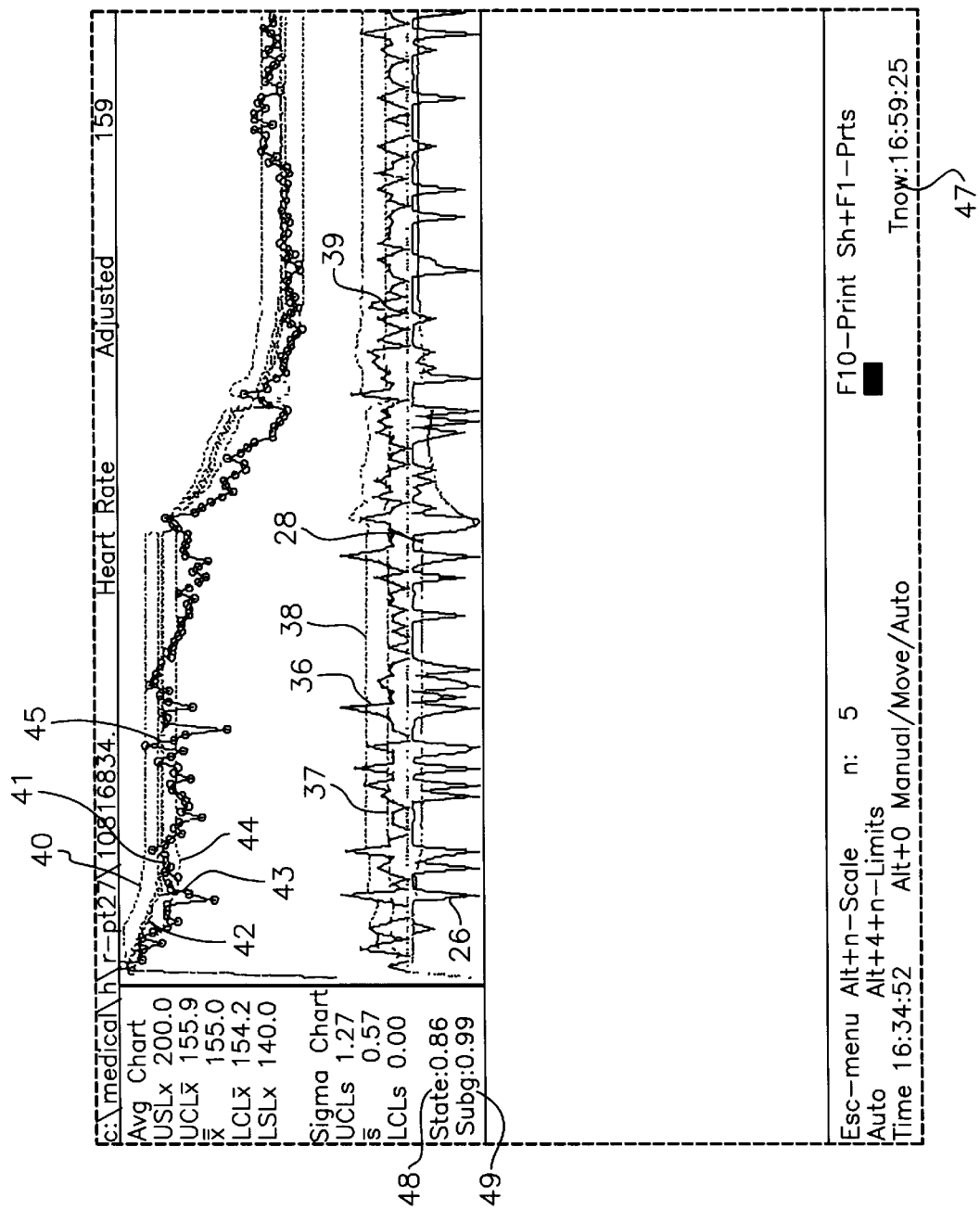
FIG. 3 illustrates part of a computer screen producing a real-time display of our homeostasis system added to the calculation and display of a Shewhart process control chart for averages and standard deviations.

In the charts shown in FIG. 3, the A–E ratio and correction factors are obtained from the following table:

TABLE 1

Formulas for the A E ratio of: Sum absolute serial difference/average subgroup sigma

| Subgroup size | Formula without truncation | Formula with truncated data |
|---|---|---|
| 3 | (Ratio - 3.0)/(-0.9) | (Ratio - 3.206)/(-1.75) |
| 5 | (Ratio - 4.84)/(-1.37) | (Ratio - 5.473)/(-3.78) |
| 10 | (Ratio - 10.63)/(-4.89) | (Ratio - 11.91)/(-9.68) |
| 20 | (Ratio - 22.57)/(-12.45) | (Ratio - 24.08)/(-21.17) |

Ratio refers to the A–E Ratio described in more detail above. Table 1 shows examples of formulas to obtain theta, the autocorrelation data. These are merely examples of how autocorrelation data may be generated.

In addition, to the linear formula, nonlinear 2nd degree polynomial formulas are useful. In particular, nonlinear formulas fit truncated data better than linear formulas. Table 3 lists examples of nonlinear formulas for the SUM absolute serial difference/average sigma. The complexity of the non-linear formula is due to the fact that it is one of the roots to a quadratic equation.

TABLE 3

Non-linear statistics

| Subgroup size | Formula without truncation | Formula with truncation |
|---|---|---|
| 3 | | $2.348 + 3.31X - 4.702 X^2$ |
| 5 | | $4.171 + 3.90X - 7.131 X^2$ |
| 10 | $10.41 - 3.9329X - 0.81182 X^2$ | $9.438 + 4.95X - 13.578 X^2$ |
| 20 | | $19.472 + 6.05X - 25.256 X^2$ |

The source of these equations are simulation. When using simulation, the number of simulations determine how close two replications agree with each other. The equation set in table 1 used 10 runs at each level. A second replication using 20 runs at each level resulted in the formula shown in Table 4.

TABLE 4

Formulas for: Sum absolute serial difference/average subgroup sigma

| Subgroup size | Formula without truncation |
|---|---|
| 10 | (Ratio - 10.56)/(-4.80) |

Examination of a graph of the formulas in Table 1 and 4 indicate that they are difficult to separate by eye.
Other suggested steps include:

13. Removing or changing the manipulation of the control limits: Another change suggested by this data is to remove this alarm and modification. For example, when six consecutive points fall within the previous control limits before the alarm the control limits may be changed back the their original;

14. Resetting control limits periodically. Similar to step 13, the limits may be reset according to the user's monitoring practices. (e.g. every shift change, the limits may be reset).

FIG. 3 illustrates part of a computer screen producing a real-time display of serial correlation 28 and average homeostasis 28 above this is a display of a Shewhart process control chart for averages 51 and standard deviations 52 as applied to neo-natal heart rate data. The data shown is actual data from a patient in a new-born intensive care unit. This continually changing average (known as a moving average 42) is accomplished in the same manner as a normal average 4 such as that used in FIG. 5 c)(i) with the exception that it is continually recalculated and re-plotted to more consistently follow patient specific data. This data is for newborns with heart rates of 2+ beats per second. Examples of subgroup sizes found to work would be subgroup sizes of 5 within 6 seconds or subgroup size of 20 within ten seconds.

In FIG. 3, the sigma chart 52 comprises an upper control limit 38, lower control limit 39, sigma (or standard deviation) 36 and an average standard deviation 37.

Below this sigma chart is the chart of the homeostasis 26 calculated using the steps 1–10 set forth above. The moving average of the homeostasis 46 is used in calculating modified upper and lower control limits 40 and 44 respectively on the subgroup average chart which is above the sigma chart. However, fewer move out of the adjusted limits 40 & 44 than limits which are not adjusted for correlation.

The subgroup average chart (average or x bar chart) s above the sigma chart and comprises a modified lower control 44, a lower control 43, a moving average (x double bar) 42, an upper control 41 and a modified upper control 40 are used to chart the subgroup average 45. This data is for an extremely unstable individual and several alarm events where the average 45 moves out of even the adjusted limits 40 and 44 are seen.

The time 47 is plotted against the data, although not displayed with each point on the charts.

There are three charts shown in this illustration. From the top down they are the x bar chart, sigma chart and theta or homeostasis chart (also shown by the designation State Subgroup).

The top chart 51 is an adjusted Shewhart process control chart for x-bar. The lines on this chart are: homeostasis adjusted upper control 40 for the process average 42, the upper control limit 41 of a process average, the process average 42 of the averages 45, the lower control 43 of a process average 42, and the homeostasis adjusted lower control 44 of the process average 42. The subgroup average 45 is the solid line that wanders up and down between the lines representing the unadjusted limits which in turn run between the adjusted control limits.

The adjusted limits 40 and 44 move in and out as a function of the value of autocorrelation which is used as a measure of homeostasis (see the discussion of the third chart below). As can be seen by looking at the top chart 51, the child being monitored at one point in time suffers a major decrease in consistency of heart rate. All of the control chart readings during this critical stage are automatically reformatted and the invention functions correctly sending alarm after alarm. However, thereafter a certain degree of autocorrelation is present. The data continues to fall outside normal limits, but remains largely within the adjusted limits. The net effect is an enhanced display with results which are more useful to the practitioner.

The second chart is a plot of the sigma chart 52 for the same information plotted in the x-bar or average chart. This sigma chart is largely a mirror image or reverse of autocorrelation since sigma 36 is a measure of change.

An alternate embodiment would use sigma limits which modify the control limits 41 and 43 utilizing sigma in place of another A–E ratio without utilizing autocorrelation 26 for uncorrelated data.

The bottom chart is the autocorrelation chart 26 which plots autocorrelation (herein used as a measure of homeostasis) 26. The value of autocorrelation 26 is graphed in the bottom chart as a function of auto-correlation from 0 to 100 percent (0 to 1). The current state or value of autocorrelation 48 is 0.86. The movement of the control limits in and out are based on this measure of autocorrelation as described below. The subgroup #49 and time 47 are also shown and recorded for later review.

Adjustments are based on the Durbin-Watson statistic which includes both a measure of changes between observations and the distance of the average from the center line-average of averages. The Durbin-Watson statistic based on a continuous stream of data is used. It is the control limit distance from the center line divided by the quantity one minus the measure of homeostasis or:

(control limit-center line)/(1-r)

where r is a the measure of autocorrelation (or homeostasis).

The formula: $(1+r^2)/(1-r^2)$ produces similar results to the prior formula and is an example of an alternate formula which may be used.

FIGS. 2(a)–2(b) show exemplary data points for heart rate data for prenatal (premature infant) patients used to generate FIG. 3. The first row shows the time when the readings are taken. The second row through the fifth row 15–19 shows the consecutive readings received from the monitoring equipment which are used to obtain a subgroup average and standard deviation as taught in Zimmerman U.S. Pat. No. 5,199,439. At the beginning of the chart shown in FIG. 1, the autocorrelation value 12 is near 1. Later in the chart it falls to the range 0.80–0.90 with occasional downward spikes below 0.6 (point six). The chart is a measure of the condition of the patient and changes in the patient's condition can be noted as they occur. The average autocorrelation stays in a more narrow range generally between 0.8 and 1 as the data is collected between subgroups 1 and 200.

Each point is plotted by taking the data points such as those shown in FIG. 2, and determining the difference of each point in a subgroup 22 relative to the next point in the subgroup or relative to the average of all of the points in the subgroup.

FIGS. 4(a)–4(d) show data similar to that shown in FIG. 2 except that the data collected in FIG. 4 is for oxygen saturation data in sleep patients used in generating charts 5(a)–5(d).

FIG. 5(a) through FIG. 5(d) are broken into two parts. Part (I) shows statistics for subgroups between 1 and 200 subgroups and part (ii) shows statistics for subgroups between 710 and 900 subgroups.

FIG. 5(a) shows the moving average 23.

FIG. 5(b) shows the standard deviation 24 for the data derived in the first chart. The standard deviation 24 is graphed with average sigma 25 against the same subgroupings 22 shown in FIG. 5(a). Sigma or standard deviation 24 runs between 0 to 16 for the successive subgroups. Average sigma 25 is shown but the upper and lower limits 5 and 6 are not adjusted.

Autocorrelation statistics: FIG. 5(c) shows the measure of Theta which is a measure of autocorrelation. The formula for this Theta is, in the preferred embodiment, derived as set forth in step by taking a ratio of a measure of serial variation to overall variation. Serial variation is a variation from one point to the next. Total or Overall variation is the overall variation of the entire sample (all subgroups). An example of overall variation is the average sigma (standard deviation). A ratio is not absolutely necessary since correlation statistics are generally only a measure of the difference between sequential points or sequential sets of points from one another. The use of a ratio, as opposed to sigma alone, only allows for a more reliable statistic. In the preferred embodiment, Serial and Overall variation is accomplished using one of the following statistics, referred to as the 'Correlation Statistics':

(1) absolute serial difference 27: graphed in FIGS. 5(d)(i) and 5(d)(ii)

absolute(pt(a)pt(b))

Where pt(a) is the first point, x, and pt(b) is the second point, $x_2$.

(2) serial difference 28:

$$\sqrt{\sum (pt(i) - pt(i+1))^2}$$

where pt(i) is the value of one data in a subgroup and pt(i+1) is the value of the next data in the subgroup;

(3) range 29: graphed in FIGS. 5(e)(i) and 5(e)(ii)

highest value of subgroup-lowest value in subgroup (4) range of first datum between successive subgroups 30:

absolute(1data point of group 1-1data point of group 2)

(5) variation between averages (averages of the subgroups) 31:

absolute(avg. subgroup 1-avg. Of subgroup 2)

(6) standard deviation within subgroups 32:

$$\sqrt{(\sum (x(individual reading) - xbar(average of subgroup))^2 / (n-1))}$$

Where n is number of observations or data points in a subgroup. The equation is summed for the individual differences.

or (7) standard deviation of all data or Total Variation 33:

$$\sqrt{(\sum (xdb - x)^2 / (N-1))}$$

Where x is an individual reading and xdb is the average of averages of all subgroups and n is number of observations or data points totaled for all the readings of data used.

Of these autocorrelation statistics, the first two are almost always used as the numerator in the ratio of serial difference to overall difference. The third can be either and the $4^{th}$ and $5^{th}$ are usually in the numerator and the $6^{th}$ and $7^{th}$ are usually in the denominator. Since the main requirement is to have a statistical measure (a statistic) of correlation, any of these alone may be used in the process described herein individually or in a ratio.

In the preferred embodiment, as taught by Durbin Watson for individual data points (versus subgroups as taught herein), a ratio may be determined by taking one of the statistics set forth above and taking the ratio of this statistic to the total variation, sigma. Sigma is the standard deviation.

FIG. 5(c) shows a graphing of theta 26, the measure of autocorrelation 26, graphed by subgroup. This measure of Theta was derived by utilizing the ratio of the absolute serial difference (Autocorrelation Statistic 1 above) against the total variation, utilizing sigma 24 which is shown graphed in FIG. 5(b). The charts do not show the graphing of the absolute serial difference.

FIGS. 5(c)(i) and (ii) show the determination utilizing a linear step function set out in detail in step 9. FIG. 5(c)(iii) shows the use of the non-linear approximation set forth in step which is the non-linear second degree polynomial method (ax^2+bx+c).

FIG. 5(c) shows how theta can be utilized to monitor data. Theta 26 can be derived in any manner as set forth above. The first 50 data subgroups show a lack of autocorrelation, each point differs from the next randomly. Then the data, theta, 26 becomes 95.7 percent autocorrelated, each data point is highly similar to the preceding data point. The standard deviation 24 disappears as each subgroup becomes similar to the preceding subgroup and the average 20 becomes consistent. Therefore FIGS. 5(a)–(c) shows the effect of correlation on data relative to the individual data points. This effect can be utilized to diagnose changes.

Individual charts reflecting this information are shown as FIGS. 5(a)(i) through 5(g). In these charts, Sigma 24 shown in 5(b) is the standard deviation of each subgroup between 0 and 100. In this example, sigma is determined for without setting an average. This analysis causes the control chart lower control limits to vary between approximately 15 and 11.

FIG. 5(b)(i) shows a modification where sigma is determined and recorded for the first 23 subgroups. These 23 subgroups are averaged. Utilizing this modification of the process, the control limits are more consistent. At subgroup 134 they are reset and the averaged to form a new adjusted level with new adjusted upper control limits and lower control limits.

FIG. 5(a)(i) shows how control limits for subgrouped data averages may be manipulated. The adjusted upper control limits 40 are not changed since a maximum of 100 percent oxygen saturation is reached for normalized data in setting the initial limits with the first 23 subgroups. The next line is the unadjusted upper control limit or upper control 41 for a process average 42. This process average is the average of the plotted subgroup averages (x double bar) for the first 23 points of subgroup averages (x-bar) 45. The next line is the unadjusted lower control 43 for the process average 42 and the bottom line is the adjusted lower control limit 44 for the process average 42. The symbols 9 show the location of individual points or individual subgroup averages.

The line for the subgroup averages wanders in and out of the unadjusted limits 41 and 43 while generally staying within the limits adjusted for correlation utilizing the process discussed above. The value of the control chart in the presence of homeostasis data is enhanced by the addition of the adjusted limits which keep most of the subgroup averages within these adjusted limits to prevent false alarms.

FIG. 5(a)(i) shows a plot of the average sub-group verses the sub-group number showing normal control limits and adjusted upper and lower control limits. FIG. 5(a)(ii) shows the same type of data shown in FIG. 5(a)(i) at a later point in time when the data becomes highly correlated.

FIG. 5(a)(i) shows how the data obtained may be used to control the limits. At approximately subgroup 134 an event occurs. The control limits 43 and 44 were altered as a result of this event which was selected as being 5 consecutive points falling outside the previous adjusted lower control 44. The adjusted control limits are determined for the first 20 subgroups after this event and the average adjustment resulting in an average for the 20 subgroups.

FIG. 5(a)(ii) shows where the control limits are reset to more narrow limits at about subgroup 742.

FIG. 5(b)(i) shows the standard deviation or sigma plotted using unadjusted control limits. Paragraph FIG. 5(b)(ii) shows the same data shown in FIG. 5(b)(i) at a later point in time.

FIG. 5(c)(i) shows a linear determination of theta where the AE ratio is determined by using the serial difference correlation statistic divided by the average of sigma for the average for all the sub-groups.

FIG. 5(c)(ii) shows the same data as shown in 5(c)(i) at a later point in time and in particular it shows how the average can be changed for the autocorrelation in a sudden drop.

FIG. 5(d)(i) and (ii) shows the graphing of the absolute serial difference correlation statistic 27 as against the subgroups with upper and lower control limits.

FIG. 5(e)(i) and (ii) shows the range of sub-group autocorrelations statistic 29. Note that the data in FIG. 5(e)(ii) shows the range correlation statistic when data becomes highly correlated.

The FIGS. 5(a)–(e) shows the average of sub-group correlation statistic graphed where the limits are determined in real time over the first 23 data points. A better estimate can be obtained over time, so these may be later stimulated using more data points (e.g.40). This may be done artificially in real time data by determining a correction of the difference between the adjusted limits an the average. In this case, multiplying this difference between the adjusted limits an the average early in the collection process by a factor of 0.5 which can be gradually removed would result in similar results. This would require a more careful monitoring of the patient initially, but this is typically the case in real time situations.

FIG. 5(f)(i) and 5(f)(ii) shows the number of standard deviations correlation statistic graph.

(1) Data is collected (2) data is separated into subgroups (3) subgroup averages are graphed after factoring in theta into these values using the formula x-m/o when x is subgrouping, m=midland chart and o is ⅓ the distance for 3 sigma limits (4) The upper and lower control limits are set at +/−3 sigma as with other control charts.

(5) Instead of adjusting the limits, here the data is adjusted.

In one embodiment, the statistic for measuring homeostasis is to take the sequential square of the difference between successive observations, as set forth above which yields the same result as the absolute serial difference. The number of sequential squares in any given group is equal to one less than the number of items in the group. Hence, it can be seen that wide variation may be made within the art without departing from the essential concepts embodied herein.

Using theta in order to derive a factor for adjusting control limits or modify data to be plotted on control charts merely envisions using the statistic for autocorrelation as a multiplier against the control limits. One method of deriving this factor is:

After collecting a series of square differences they are summed divided by the degrees of freedom (group-2) and multiplied by a conversion formula. Four examples of these correlation factors are:

(1)
$$= \frac{19.5 - \text{Sqrt(statistic)}}{2*4.6}$$

(2)
  1/(1-theta)
(3)
  1/(sqrt(1-theta^2)
(4)
  (1+theta^2)/(1-theta^2).

The purpose behind these various analysis are to force control chart data to conform to the theory that actual control limits for autocorrelated data (where each point is related to the preceding point) should be approximately equal to control limits for statistically independent data (data which has no correlation, such as a dice roll).

This statistic was derived from an analysis of the homeostasis behavior. It is a non-linear approximation. A linear approximation as well as any number of other formulas may be derived to perform this task. When using the between group calculation method, a special formula is required as a function of group size.

FIG. 8 shows how this process gives desired results. FIG. 8 shows where correlated data 50 is plotted with the A–E ratio against the value stipulated for correlation between 0 and 1. Against this actual data, a linear derivation of the A–E ratio 51 and a non-linear derivation 52 of the A–E ratio are plotted.

The doser plot between correlations between 60 and 100 percent in this case is the non-linear derivation 52 and it is therefore used. However, a linear derivation may be better between correlations of zero to 60 percent where the data 50 is of a more linear nature.

When process control charts are used, the incorporating the process can be defined with the following steps:
 1. producing control charts through the process of:
  (a) collecting said data from said monitoring device (Selecting the specific data associated with a given quality characteristic such as oxygen saturation from the data stream);
  (b) placing said data into statistically significant subgroups of at least one datum each;
  (c) calculating for said statistically significant subgroups statistics to graph against said control charts;
  (d) repeating the process steps (a) through (c) continuously;
  (e) selecting for a statistically significant number of repetitions of steps (a) through (c) the data necessary to set at least one control chart limit;
  (f) setting at least one control chart limit with said data;
  (g) setting up at least one control chart with said at least one control chart limit;
  (h) continuously graphing said statistics against said at least one control chart making a diagnosis or performing a treatment on said patient using said monitored vital signs graphing statistics.
 2. Determining the level of consistency in the data (homeostasis in the said patient data) using autocorrelation calculations on the data gathered in step 1 (a) to produce a numerical or analog result;
 3. calculating a statistic to adjust the control limits of Shewhart process control charts, or other process control charts such as the cumulative sum charts, exponential weighted moving average charts, grand mean moving average charts, or continuous hypothesis testing process control chart;
 4. adjusting the process control chart control limits for the presence of homeostasis for medical decision making and analysis.
 5. graphing the numerical result on screen or paper in real-time as the data are collected or after-the-fact for case review (Dynamically or statically displaying the results of the analysis on screen paper or other media). The graph includes individual results and an average. The homeostasis scale is 0 to 1, however, alternative scales may be used.
 6. Maintaining a database of the results so that the data may be played back dynamically, printed on paper, or transferred to other programs for additional analysis.

Significant outliers are distinguished from other outliers. This is done by taking adjusted control limits and only examining data when it falls within a certain distance of certain changes in the adjusted control limits or when it falls outside of the adjusted control limits. The limits are adjusted as a function in changes in boiler plate autocorrelation. The limits may be readjusted when the data returns to a prior steady state.

The step of displaying the control chart statistic for the patient specific reading might include displaying the correlation value determined for the patient specific reading for each subgroup data. The step of displaying serial correlation further comprises the step of (a) determining a set of events for re-determination of the correlation value and (b) re-determining the correlation value and correcting factor to obtain a new correcting factor when the set of events for re-determination occurs. Examples of when this would occur when there are a selected number of data points falling outside of the modified control limits, a selected number of consecutive or near consecutive points falling outside of the modified control limits, determining an acceptable difference between the average and the control limits and obtaining a factor of that acceptable difference and (b) modifying the correlation value when this acceptable difference is exceeded; or making the change based on a set event not associated with the condition of the patient, such as the passage of a certain amount of time, the change of nurses, a length of time from a proceedure on the patient, etc.

In some cases, such as a healthy patient going into surgury, the step of recording the correlation value and displaying the control chart using the old correcting factor might include recording this value and, when a statistically significant number of consecutive points fall within these original control limits, returning to the original correction factor and modified limits.

For patients without their own stablized data, it may be desirable to include in the step of modifying the value of the control limits in charts where data is displayed by computing a new value for the control chart limits as a factor of the correlation statistic with an additional step of (1) storing correcting factors for different stored serial correlation values (2) matching a stored value with a value for serial correlation determined for the data and (3) computing a new value for the control chart limits as a factor of the selected stored value.

Similarly, in order to take full advantage of the knowledge of the dynamic changes in the correlation value where this is being changed regularly, it would be helpful to display the unadjusted limits contemporaneously with the adjusted limits correlating the results with interpretations of what the results show.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed is:

1. A method of evaluating patient specific data from a medical monitor which measures patient vital signs readable as individual data readings having a value as of a particular relevant time comprising of the steps of:

a) selecting individual data readings;
   b) setting a subgroup number as the number of measurements in subgroups;
   c) grouping the data readings so that a number of readings equal to the subgroup number are grouped into consecutive subgroups as subgroup data;
   d) determining at least one control chart statistic for each of the subgroups;
   e) determining a correlation value for correlation between at least two individual data readings;
   f) determining at least one control chart limit;
   g) determining at least one correcting factor for modifying the at least one control chart limit relative to the correlation value;
   h) modifying the at least one control chart limit using the at least one correcting factor to obtain a modified chart limit;
   i) displaying the at least one control chart statistic for the patient specific data in conjunction with the at least one modified chart limit.

2. The method of claim 1 wherein each individual data reading is taken at a relevant time, said relevant time being the time when the data reading is taken and wherein the step of selecting individual data readings further comprises (a) associating at least one data reading with the relevant time for that data reading and wherein the step of displaying the at least one control chart statistic for the patient specific data further comprises (a) displaying the at least one control chart statistic data associated with the relevant time associated with the at least one data reading from the subgroup from which the control chart statistic is determined.

3. The method of claim 2 wherein the step of determining a correlation value between at least two individual data readings further comprises the steps of:

a) setting a correlation subgroup number as the number of measurements in subgroups;
   b) grouping the data readings so that a number of readings equal to the correlation subgroup number are grouped into consecutive subgroups as subgroup data;
   c) determining a correlation value between at least one control chart statistic of one subgroup with the same at least one control chart statistic of another subgroup.

4. The method of evaluating patient specific data of claim 2 wherein the step of determining a correlation value comprises the additional steps of:

(a) determining a first correlation statistic for the at least two consecutive data readings;
   (b) determining a second correlation statistic for the at least two consecutive data readings;
   (c) determining a ratio of the first correlation statistic to the second correlation statistic as the correlation value.

5. The method of claim 4 wherein the step of determining the second correlation statistic further comprises determining at least one first correlation statistic from the selected group consisting of:

(1) absolute serial difference;
   (2) serial difference;
   (3) range;
   (4) range of first datum between successive subgroups;
   (5) variation between averages (averages of the subgroups);
   (6) standard deviation within subgroups; and
   (7) standard deviation of all data.

6. The method of claim 4 wherein the step of determining a first correlation statistic further comprises determining at least one first correlation statistic from the selected group consisting of:

(1) absolute serial difference;
   (2) serial difference;
   (3) range;
   (4) range of first datum between successive subgroups;
   (5) variation between averages;
   (6) standard deviation within subgroups; and
   (7) standard deviation of all data.

7. The method of claim 4 wherein the step of determining the ratio of correlation statistics further comprises determining a ratio of correlation statistics for the data subgroups.

8. The method of claim 7 wherein the step of determining a ratio comprises the step of making a ratio of an absolute serial difference statistic divided by a standard deviation statistic.

9. The method of claim 4 wherein the step of determining a ratio of correlation statistics comprises the step of preparing a ratio of a serial variation statistic to a total variation statistic.

10. The method of claim 2 wherein the step of determining a correlation value further comprises:

(a) assigning a correlation value for an acceptable level of serial correlation based upon the desired level of homeostasis in the patients condition.

11. The method of claim 2 wherein the step of determining at least one correcting factor further comprises the step of:

(a) setting the value of the correcting factor for an assigned acceptable level of serial correlation so that when acceptable patient specific data is displayed on the control chart it falls within the modified control limits.

12. The method of claim 2 wherein the step of displaying the at least one control chart statistic for the patient specific reading further comprises the step of displaying the value for correlation determined for the patient specific reading for each subgroup data.

13. The method of evaluating patient specific data of claim 1 utilizing patient data from control data from control patients whose treatment was considered successful wherein the step of determining a correlation value comprises the additional steps of:

(a) collecting control data from control patients;
    (b) grouping the control data into statistically significant control subgroups of control subgroup size of at least one data point of a size wherein the control subgroup size is statistically significant to the subgroup number of the subgroup of the patient specific data;
    (c) Determining at least one control chart statistic for control subgroups of the data identical to the statistics of the patient individual data readings to be examined;
    (d) determining a control correlation statistic for the control subgroups of control data;
    (e) and wherein determining the at least one correcting factor further comprises determining the correction value relative to the control correlation statistic.

14. The method of claim 13 wherein the control data is from statistically derived hypothetical-patient data as opposed to live patient data.

15. The method of claim 13 wherein grouping by correlation further comprises grouping by the amount of serial correlation in assigned increments of serial correlation.

16. The method of claim 13 wherein the step of determining a correcting factor further comprises performing regression analysis of the statistics determined using the control data.

17. The method of claim 16 wherein the step of performing regression analysis further comprises:

(a) graphing the A–E ratio against corresponding incremental values of serial correlation;

(b) performing a standard regression from the following list of regression analysis linear sum of least squares or non-linear sum of least squares to fit the average A–E ratio to the assigned value of serial correlation for the control data to determine a specific factor in the form of a formula which formula approximates the line formed by graphing the a–e ratio to input serial correlation.

18. The method of evaluating patient specific data of claim 1 wherein the the at least one control chart statistic and at least one control chart limit form a control chart comprised of a chart from the selected group consisting of: Shewhart process control charts; the cumulative sum chart, exponential weighted moving average chart, grand mean moving average chart, and continuous hypothesis testing process control chart.

19. The method of claim 1 wherein the step of displaying serial correlation further comprises the step of (a) determining a set of events for redetermination of the correlation value and (b) re-determining the correlation value and correcting factor to obtain a new correcting factor when the set of events for redetermination occurs.

20. The method of claim 19 wherein the step of determining a set of events and re-determining the correlation value further comprises modifying the control limits as a factorof the serial correlation value when there are a selected number of data points falling outside of the modified control limits.

21. The method of claim 20 wherein the selected number of data points are consecutive points falling outside of the modified control limits.

22. The method of claim 19 wherein the step of modifying the control limits further comprises the step of (a) determining an acceptable difference between the average and the control limits and obtaining a factor of that acceptable difference and (b) modifying the correlation value when this acceptable difference is exceeded.

23. The method of claim 19 wherein the set of events is further determined based on a set event not associated with the condition of the patient.

24. The method of claim 1 wherein the at least one control chart statistic of the patient specific data further comprises the average and standard deviation for the patient specific data.

25. The method of claim 1 wherein the step of (b) modifying the value of the control limits in charts where data is displayed by computing a new value for the control chart limits as a factor of the correlation statistic comprises (1) storing correcting factors for different stored serial correlation values (2) matching a stored value with a value for serial correlation determined for the data and (3) computing a new value for the control chart limits as a factor of the selected stored value.

26. The method of claim 1 wherein step f further comprises saving the control chart limit as an unadjusted limit and further compromising the step of displaying the unadjusted limit contemporaneously with the modified chart limit.

* * * * *